United States Patent [19]

Miller et al.

[11] Patent Number: 5,731,471
[45] Date of Patent: Mar. 24, 1998

[54] PROCESS FOR THE PREPARATION OF 2,3-PENTANEDIONE

[75] Inventors: Dennis J. Miller, Okemos; James E. Jackson, Haslett, both of Mich.; Robert H. Langford, Lafayette, Ind.; Garry C. Gunter, Houston, Tex.; Man Sang Tam, East Lansing; Prashant B. Kokitkar, Lansing, both of Mich.

[73] Assignee: Board of Trustees operating Michigan State University, East Lansing, Mich.

[21] Appl. No.: 547,932

[22] Filed: Oct. 25, 1995

[51] Int. Cl.$^6$ ............................................. C07C 45/00
[52] U.S. Cl. ............................................................. 568/397
[58] Field of Search ............................................ 568/397

[56] References Cited

U.S. PATENT DOCUMENTS 2,859,240  11/1958  Holmen et al. .......................... 260/486
4,729,978  3/1988  Sawicki .................................. 502/174

OTHER PUBLICATIONS

Gunter, et al., J. Of Catalysis 148 252–250 (Jun.–Jul. 1994).
Gunter, et al., Ind. Eng. Chem. 34 974–980 (1995).
Biomass conference 1298–1304 (Aug.30–Sep. 2, 1993).
Abstract, 9th CFMR/Industry Symposium (Apr. 1995).
13th North Amer. Meeting of Catalysis Soc. (May 1993).
AIChE (Fall 1992).
Corn Utilization Conference (1992).
Proc. 14th North American Meeting of Catalysis Society (Jun. 1995).
AIChE Meeting (Nov. 1994).
Corn Utilization Conference (Jun. 1994).
Perry et al., Chemical Engineer's Handbook, 5th ed., McGraw–Hill Book Co., New York, (1973), pp. 13–36–13–42.

*Primary Examiner*—Paul F. Shaver
*Attorney, Agent, or Firm*—Ian C. McLeod

[57] ABSTRACT

A process for the preparation of purified 2,3-pentanedione from lactic compound which is lactic acid or a lactic acid ester. The process uses elevated temperatures between about 250° to 370° C. for heating a support (catalyst 16) and pressures between about 0.1 to 10 MPa to produce the 2,3-pentanedione in a reaction mixture. The lactic compound is converted primarily to 2,3-pentanedione, acrylic acid, and acetaldehyde at the elevated temperatures over the catalyst. The 2,3-pentanedione is preferably separated from the reaction mixture as an azeotrope with water at about 80° to 90° C. and then cooled to separate the 2,3-pentanedione from the water.

11 Claims, 11 Drawing Sheets

PROCESS FOR THE PREPARATION OF 2,3-PENTANEDIONE

GOVERNMENT RIGHTS

This invention was made with government support under Grant No. NRI 93-37500-9585 by the United States Department of Agriculture. The government has certain rights in the invention.

BACKGROUND OF THE INVENTION

(1) Summary of the Invention

The present invention relates to a process for the preparation of 2,3-pentanedione by reacting lactic acid on a catalyst at elevated temperatures and then separating the 2,3-pentanedione by a unique process step which relies upon azeotropic distillation of the 2,3-pentanedione and water from the reaction mixture and cooling to separate the 2,3-pentanedione from the water. In particular, the present invention relates to a process which uses a particular group of potassium and cesium compounds as catalysts to unexpectedly produce the 2,3-pentanedione in high overall yield and selectivity.

(2) Description of Related Art

Lactic acid (2-hydroxypropanoic acid) is a bifunctional, optically active molecule traditionally used as a food additive and in textile production. It is produced by starch-based fermentation processes, and can have applications in biodegradable polylactide polymers.

2,3-Pentanedione is a high-value fine chemical currently produced in limited quantities ($\sim 4 \times 10^3$ kg/year) through a multistep chemical synthesis or by recovery from dairy waste. It is used primarily as a flavoring ingredient but has potential for applications as a feedstock, solvent and as a photoinitiator for polymers.

Primary pathways of lactic acid chemical conversion are shown in FIG. 1. Direct dehydration of lactic acid to acrylic acid has long been of interest as a potential route to polymers from biomass, and most lactic acid conversion processes have focussed on this reaction. U.S. Pat. Nos. 2,859,240 to Holmen et al and 4,729,978 to Sawicki describe the formation of acrylic acid.

The formation of 2,3-pentanedione from lactic acid over catalysts, particularly sodium salts and bases is described by some of the inventors herein in Gunter, et al., J. of Catalysis 148 252–260 (June–July 1994). Some of the inventors herein discuss this conversion in a Biomass conference 1298–1304 (Aug. 30–Sep. 2, 1993). Other abstracts are: Proc. 14th North American Meeting of Catalysis Society (June 1995); AIChE Meeting (November 1994); Corn Utilization Conference (June 1994); 13th North Amer. Meeting of Catalysis Soc (May 1993); AIChE (Fall (1992); Corn Utilization Conference (1992); Proc. 12th Corn Utilization Conference, St. Louis, Mo. (June 1994). In these publications the 2,3-pentanedione was produced, but a separation process was not described. The best yields and selectivities (Table 2 of Gunter et al (1994) and Tables 1 to 4 of Gunter et al (1995)) were with sodium phosphate, sodium nitrate, sodium arsenate, sodium hydroxide, sodium hydrogen phosphate and all were too low to be economic. There was a need for yields which made the process economically viable. An additional problem was that there was a need for a separation step to remove the 2,3-pentanedione from the reactant lactic acid and numerous by-products of the reaction.

OBJECTS

It is therefore an object of the present invention to provide an improved process for the production of a purified 2,3-pentanedione from lactic acid, wherein a clean separation of the 2,3-pentanedione is achieved. It is particularly an object of the present invention to provide a process which is relatively easy to perform, is economical and produces the 2,3-pentanedione in high overall yield and selectivity. These and other objects will become increasingly apparent by reference to the following description and the drawings.

DESCRIPTION OF PREFERRED EMBODIMENTS

Figure 1:
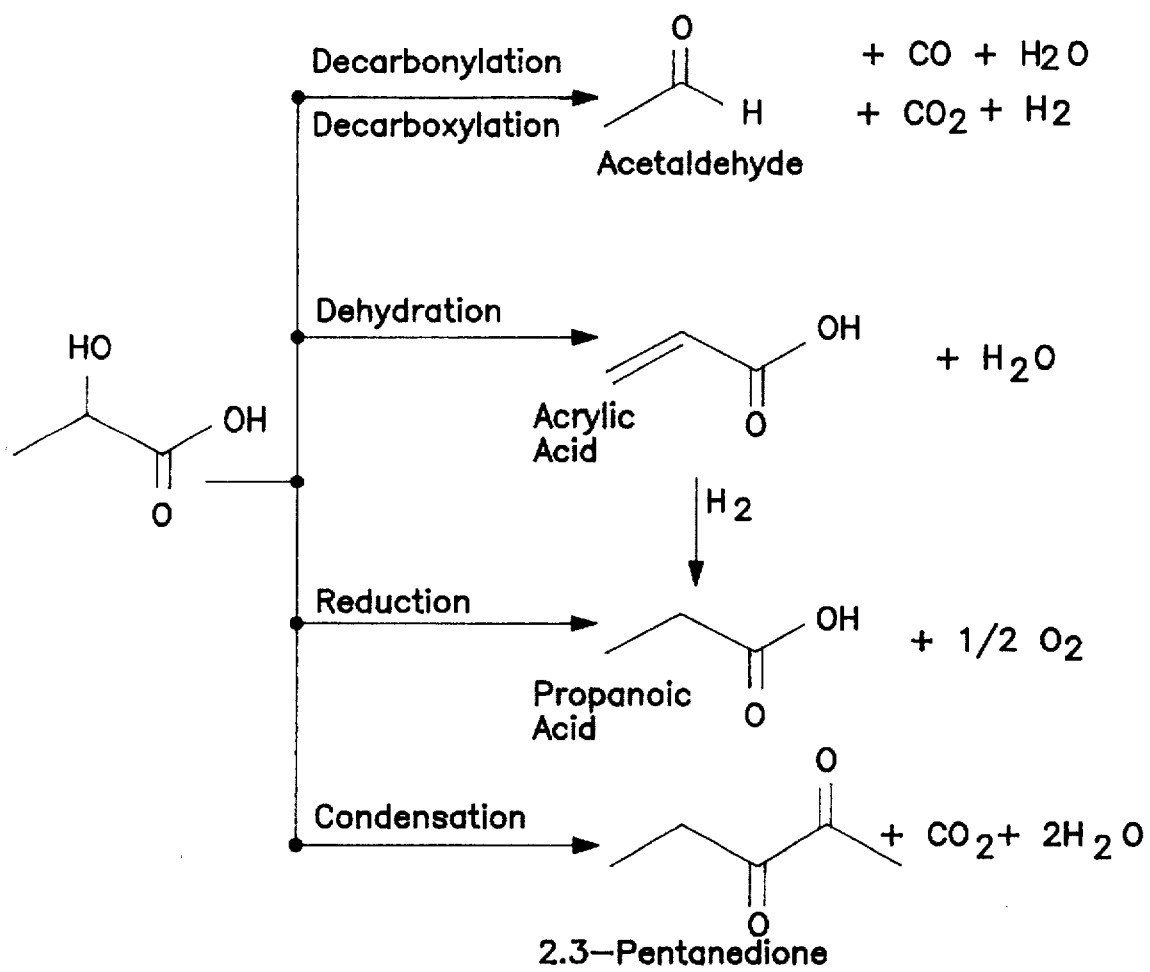
FIG. 1 is a schematic diagram showing various conversions of lactic acid described in the prior art, particularly a condensation reaction to 2,3-pentanedione, as well as the major by-products of the condensation to form 2,3-pentanedione.

The present invention relates to a process for the preparation of 2,3-pentanedione which comprises contacting a lactic compound selected from the group consisting of lactic acid and lactic acid alkyl esters wherein alkyl contains 1 to 6 carbon atoms in a reaction mixture with a support in the presence of a non-reactive gas at a temperature, wherein the support is heated to between about 250° to 370° C., and at pressures between about 0.1 and 10 MPa, and wherein the contacting is for a period of time which converts the lactic compound to 2,3-pentanedione; separating the 2,3-pentanedione from the reaction mixture by distillation of the reaction mixture between about 80° to 90° C. to distill an azeotropic mixture of the water and the 2,3-pentanedione from the reaction mixture; and cooling the azeotropic mixture to separate the 2,3-pentanedione from the water.

The present invention relates to a process for the preparation of 2,3-pentanedione which comprises contacting lactic acid in a reaction mixture containing less than about fifty percent (50%) by weight of the lactic acid in water on a support in the presence of a non-reactive gas at a temperature, wherein the support is heated to between about 250° and 370° C. and at pressures between about 0.1 and 10 MPa and wherein the contacting is for a period of time which converts the lactic acid to 2,3-pentanedione; separating the 2,3-pentanedione from the reaction mixture by distillation of the reaction mixture between about 80° to 90° C. to distill an azeotropic mixture of water and the 2,3-pentanedione from the reaction mixture; and cooling the azeotropic mixture to separate the 2,3-pentanedione from the reaction.

The present invention also relates to a process for the preparation of 2,3-pentanedione which comprises: contacting a lactic compound selected from the group consisting of lactic acid and lactic acid alkyl esters, wherein alkyl contains 1 to 6 carbon atoms in a reaction mixture with a support containing an inorganic compound selected from the group consisting of potassium and cesium salts and bases and mixtures of the salts and bases in the presence of a non-reactive gas, at a temperature wherein the support is heated to between about 250° and 370° C. and at pressures between about 0.1 and 10 MPa and wherein the contacting is for a period of time which converts the lactic compound to 2,3-pentanedione with an overall yield of at least about 40% and a selectivity of at least about 60%; and separating the 2,3-pentanedione from the reaction mixture.

Further the present invention relates to a process for the preparation of 2,3-pentanedione which comprises: contacting lactic acid in a reaction mixture containing less than about fifty (50) percent by weight of the lactic acid in water on a support containing inorganic compound selected from the group consisting of potassium and cesium salts and bases and mixtures of the salts and bases in the presence of a non-reactive gas at a temperature wherein the support is heated to between about 250° and 370° C. and at a pressure between about 0.1 and 10 MPa and wherein the contacting is for a period of time which converts the lactic acid to 2,3-pentanedione with an overall yield of at least 40% and a selectivity of at least about 60%; and separating the 2,3-pentanedione from the reaction mixture. The general reaction was discussed by the inventors in Abstract, 9th CFMR/Industry Symposium (April 1995).

Preferably the support is a ceramic support having a surface area between about 1 and 500 square meters per gram. The surface is preferably coated with an inorganic compound such as an alkali metal salt or base which acts as a catalyst and which is preferred. Most preferably potassium or cesium salts, particularly phosphates, nitrates and hydroxides are used. Other salts are arsenates and antimonates. Potassium and cesium hydroxide can be used with particularly good results. Mixtures of salts as well as salts and bases can be used.

The temperature of the surface is between about 250° C. and 370° C.; most preferably 280° to 300° C. The pressure is preferably between about 0.1 and 1.0 MPa, most preferably between about 0.4 and 0.8 MPa where 0.1 MPa is 1 atmosphere. The surface is contacted by the lactic compound aqueous solution for about 0.1 to 10 seconds.

The lactic acid (or ester thereof) solution preferably contains less than about fifty (50) percent lactic acid in water to prevent clogging of the surface. Most preferably the aqueous solution contains between about 30 and 40 percent by weight lactic acid (or ester thereof). Where a batch process is performed, higher amounts of 2,3-pentanedione can be used up to the pure compound. With a continuous process in a reactor plugging is avoided by using water.

Figure 2:
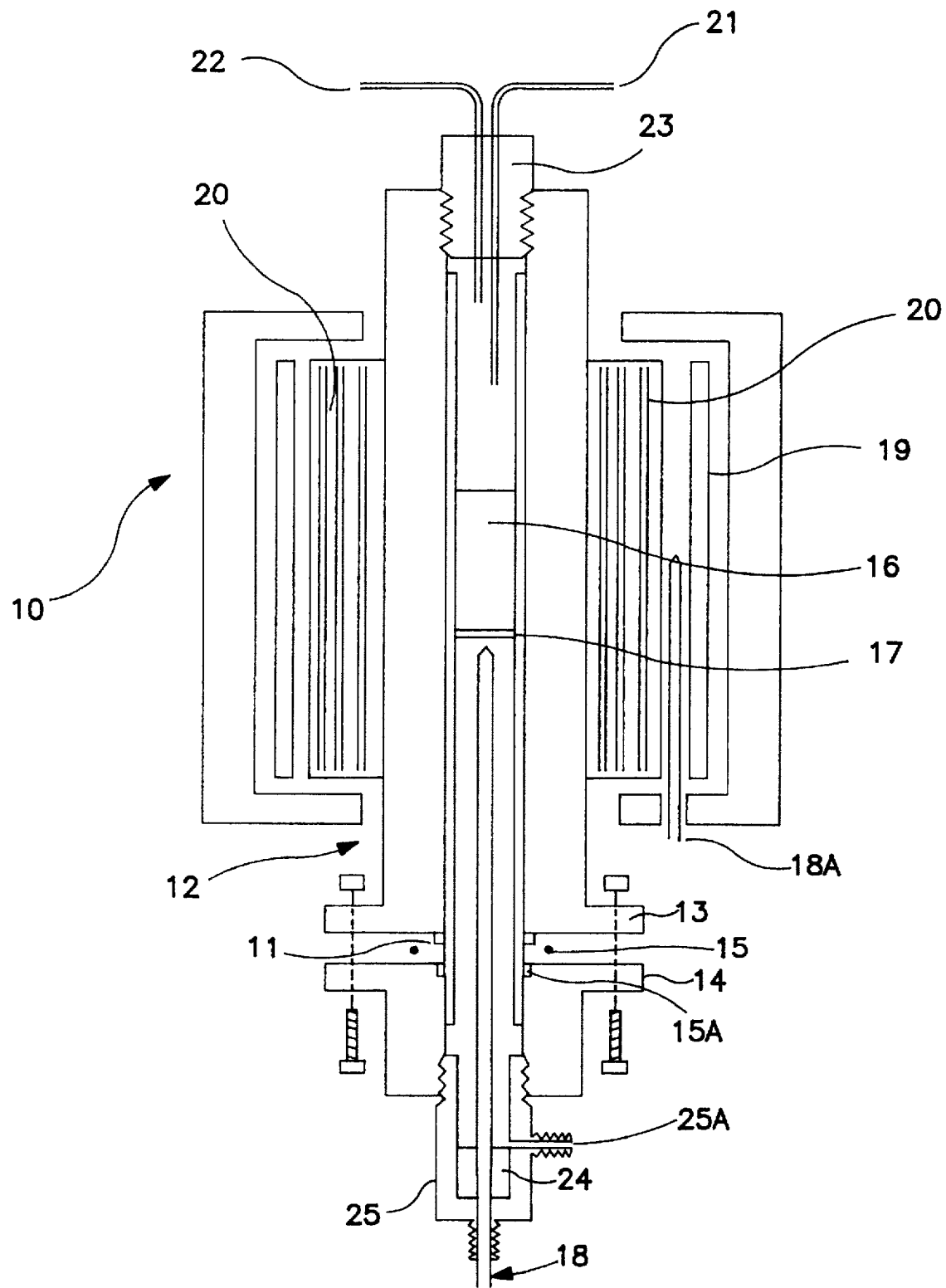
FIG. 2 is a schematic diagram showing a vapor phase reactor 10 for producing 2,3-pentanedione as described in the prior art.
Figure 2A:
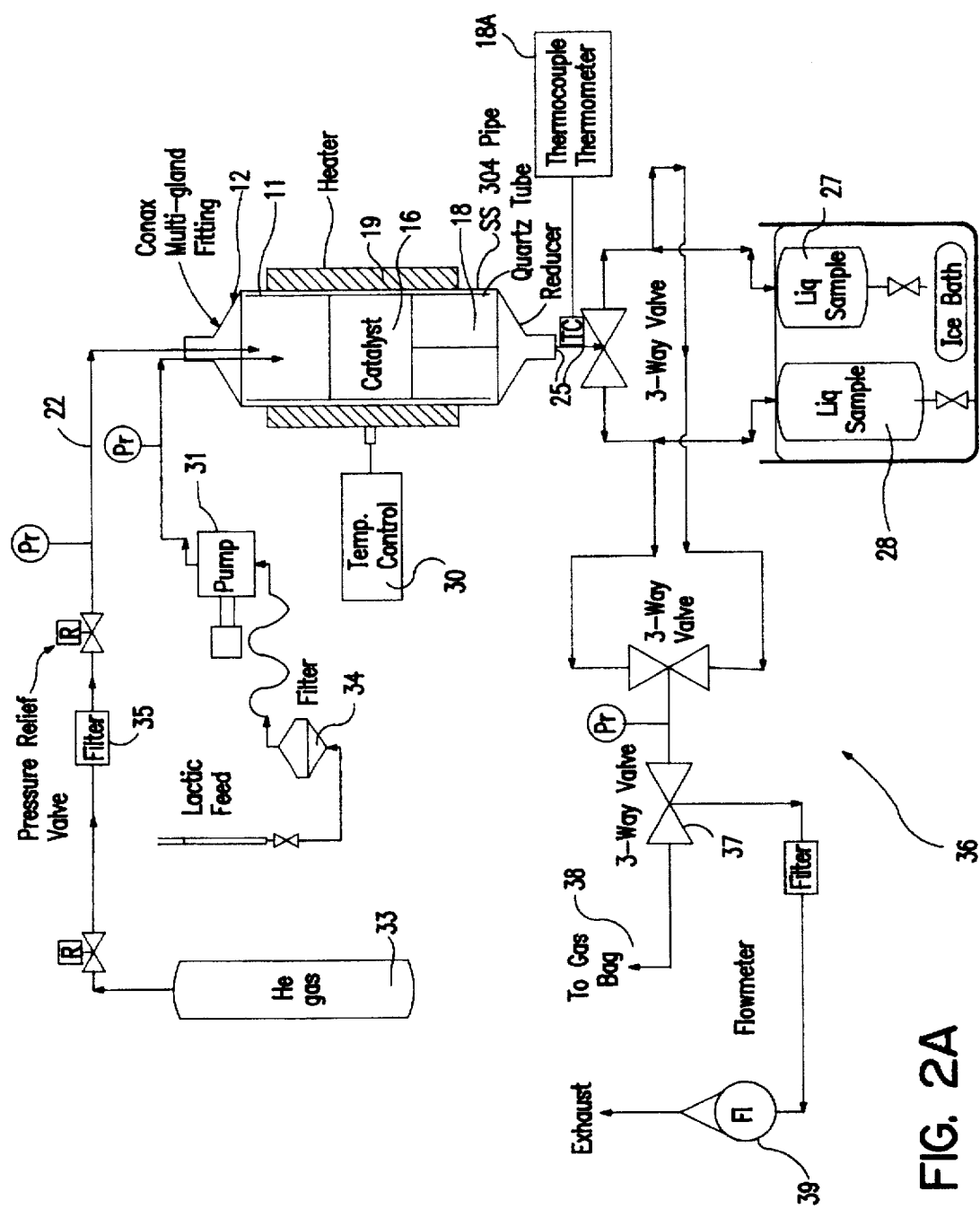
FIG. 2A is a schematic diagram showing the reactor 10 in an operative setting for the conversion of lactic acid to 2,3-pentanedione.

The vapor-phase reactor apparatus 10 used to convert lactic acid (or ester thereof) to 2,3-pentanedione is shown in FIGS. 2 and 2A. FIG. 2 is described in the Gunter et al publication (1994) discussed above. A vertical, down-flow packed bed reactor 10 was equipped with a quartz liner tube 11. The vertical orientation was found preferable to other orientations, since a horizontal reactor led to coking and poor product recovery as a result of incomplete lactic acid vaporization. The use of a metal liner led to undesirable lactic acid conversion to acetaldehyde and propanoic acid. The reactor body 12 consisted of a 316 stainless steel tube 19.5 inches (49.5 cm) long, 1.25 in. (3.18 cm) o.d. and 0.55 in. (1.4 cm) i.d. A flange closure 13, 14 at the bottom of the reactor body 12 is sealed by a spring-loaded metal seal 15 and 15A (Helicoflex, Columbia, S.C.) which facilitates internal access. The reactor 10 is designed for pressures up to 5 MPa at a temperature of 500° C. A support (catalyst) 16 is mounted on a coarse quartz frit 17 fused into the 19-in. (48.3 cm) long×0.50 in. (1.27 cm) i.d. quartz liner tube 11, which is inserted into the reactor body 12 from the bottom and sealed to the flange 14 to prevent gas bypass. An internal quartz thermocouple well 18 extends from the reactor flange to the bottom of the support frit 17 to measure reaction temperature. The reactor body 12 is heated by a clamshell electric heater 19 controlled by a programmable temperature controller 30 (FIG. 2A) with an outside control thermocouple thermometer 18A. A 6.5 in. (16.5 cm) long and 0.5 in. (1.27 cm) thick copper heat sink 20 surrounds the reactor 10 in the heated zone to minimize temperature gradients. During operation, support temperature is measured by the internal thermocouple by instrument 18A (FIG. 2A), and the reactor 10 set point is adjusted to achieve the desired values. The reactor apparatus 10 ends are heated by flexible heat tape (not shown) to prevent product or lactic acid condensation. Stainless steel liquid tube 21 and gas feed tube 22 (0.062 in. (0.16 cm) o.d.) enter the top of the reactor through a Conax (Conax Buffalo Corporation, Buffalo, N.Y.) fitting 23 and extend well inside the quartz liner tube 21. Liquid feed solutions are pumped with an Eldex (Napa, Calif.) HPLC metering pump 31, and helium from source 33 is used as an inert gas to flush the reactor apparatus 10 and dilute the feed during reaction. A Teflon spacer 24 supports the inside thermocouple 18. The effluent exits from opening 25A of fitting 25. The effluent can be collected in tanks 27 or 28 for analysis. Most usually it is processed to separate the 2,3-pentanedione from the water. In FIG. 2A, Pr is a pressure valve and R is a pressure relief valve. A filter 34 is used to remove particulates from the lactic acid (or ester thereof) feed. A filter 35 is used to filter the helium.

The 2,3-pentanedione is preferably separated from the reaction mixture by distillation as an azeotrope at elevated temperatures between 80° and 90° C. The 2,3-pentanedione separates from water and other reaction products upon cooling. Additional separation can be performed to remove any 2,3-pentanedione in the water.

In the Examples, yield is defined as percent of the theoretical yield for condensible products; CO and $CO_2$ yields are reported as mol of gas evolved/100 mol of lactic acid fed to the reactor. Selectivity, which is reported in parentheses in Tables 3, 4 and 5, is defined as the percent of converted lactic acid which goes to the specified condensible product.

EXAMPLE 1

PRIOR ART MATERIALS AND METHODS

This Example uses the procedure of Gunter et al (1994) to prepare 2,3-pentanedione in the conversion reaction of FIG. 1.

Lactic acid feed (Aldrich, Milwaukee, Wis., 85 wt %) was diluted to 34 wt % to simulate a typical refined lactic acid fermentation product. High purity acrylic acid, 2,3-pentanedione, propanoic acid, acetaldehyde, hydroxyacetone, and other chemicals were used as calibration standards.

Sodium phosphate salts ($NaH_2PO_4 \cdot H_2O$, $Na_2HPO_4 \cdot H_2O$, $Na_3PO_4 \cdot 12H_2O$, Aldrich) were deposited onto a low surface area silica-alumina support by wet impregnation and drying for 24 hours at 100° C. The support (93% $Al_2O_3$, 7% $SiO_2$, Johnson-Matthey) had a surface area of 5 $m^2/g$ as measured by $N_2$ BET analysis; as-received support pellets (2-mm extrudate) were crushed and sieved to −16+30 mesh prior to impregnation. Unless noted otherwise, all catalyst loadings were 0.001 mol/g of support.

Monosodium and disodium phosphates undergo dehydration upon heating. Dehydration of $NaH_2PO_4$ to sodium acid pyrophosphate ($Na_2H_2P_2O_7$) occurs around 200° C., and further dehydration to linear or cyclic sodium metaphosphate $(NaPO_3)_n$ occurs at 260°–300° C. Dehydration of $Na_2HPO_4$ to give sodium pyrophosphate ($Na_4P_2O_7$) occurs around 260° C. $^{31}$P MAS NMR of supported sodium phosphate salts following heating to 300° C. for 1 hour was conducted; the spectra obtained, upon comparison with literature spectra, indicate that $NaH_2PO_4$ and $Na_2HPO_4$ fully dehydrate upon heating to 300° C. The species present at the onset of reaction are therefore $(NaPO_3)_n$, $Na_4P_2O_7$, and $Na_3PO_4$ for the mono-, di-, and tribasic sodium phosphates, respectively.

Biomineral-derived calcium hydroxyapatite was also investigated on a limited basis as a potentially inexpensive phosphate catalyst. This catalyst was prepared by calcination of bovine teeth in air at 800° C. for 4 hours to remove organic matter, and then crushed to −16+30 mesh. The $N_2$ BET surface area of the hydroxyapatite was 6 $m^2/g$ following preparation. The MAS $^{31}$P NMR spectrum of the prepared hydroxyapatite gave essentially a single peak, illustrating the homogeneity of the material.

Products of reaction exited the bottom of the reactor apparatus 10 at opening 25A and passed first through a 10-ml stainless steel trap or tank 27 or 28 placed in an ice bath. Non-condensible products flowed through a metering valve 37 and a flowmeter 39 and were collected in a gas collection bag 38. Typically, products were collected for a specified period of time (10–120 min) during steady-state operation of the reactor 10; the volume of liquid product and gas product collected was measured during steady-state operation in order to conduct an overall mass balance. During transient periods of operation, liquid products were condensed in a waste trap and gases were exhausted to a fume hood (not shown). All traps or tanks 27 and 28 and exit lines are cleaned between runs.

Analysis of condensible products was performed using a 4% Carbowax/Carbopack B-DA (Supelco, Bellefonte, Pa.) packed column in a Varian 3700 gas chromatograph (Palo Alto, Calif.) with flame ionization detection (FID). Crude condensed effluent was filtered using disposable syringe filters to remove the small quantity of particulates present, then mixed with a solution containing 2-propanol as an internal standard and oxalic acid as a column conditioner. Good reproducibility of the lactic acid analysis was achieved by injecting 1-μl samples directly onto the column and leaving the syringe in the injector for 1 minute. This assures complete lactic acid vaporization and results in linear calibration curves for lactic acid.

Major products analyzed included acrylic acid, propanoic acid, 2,3-pentanedione, acetaldehyde, and hydroxyacetone (acetol). Minor products included ethanol, acetone, acetic acid, methyl acetate, pyruvic acid and several unknowns; together these minor products were reported as "Other" in the results. All product yields were calculated from ratios of product-to-internal standard peak areas and detector response factors. Product identification, particularly for 2,3-pentanedione, was conducted by matching of residence time with standards, by gas chromatography/mass spectroscopy, and by $^1$H NMR.

Gas samples were analyzed using a Spherocarb column in a Perkin-Elmer 3400 gas chromatograph (Norwalk, Conn.) with thermal conductivity detection. Gas products analyzed included CO, $CO_2$, methane, ethane, ethylene, and acetylene. Yields of CO and $CO_2$ are reported as mole of gas per mole lactic acid fed.

Peak areas from GC analyses, liquid and gas product volumes, and feed flow rate and concentration were entered into a spreadsheet program which calculates product yields, selectivities, and the overall carbon mass balance for the experiment. Product yield was reported as a percentage of the theoretical yield based on lactic acid fed to the reactor; product selectivity was the percentage of theoretical yield based on lactic acid reacted to products. Typically, the overall carbon balance gave recoveries ranging from 85 to 105%.

Each catalyst loaded into the reactor apparatus 10 was tested at several temperatures and residence times in a given experiment. The catalyst was first heated in helium until the temperature reached 280° C., at which time lactic acid solution was fed at a relatively high flow rate (0.5 ml/min). Once product flow was established, helium and lactic acid solution flow rates were adjusted to desired values and the system was allowed to reach steady state. Reactor effluent was then directed to the product collection trap 27 or 28 and gas bag 38 for a specified time period of collection. The process was repeated at each set of reaction conditions. A compilation of experimental conditions is given in Table 1.

TABLE 1

| Reaction Conditions | |
|---|---|
| Temperature (°C.) | 250–375 |
| Pressure (MPa) | 0.5 |
| Liquid flow rate (ml/min) | 0.05–0.5 |
| Helium flow rate (ml/min) | 10–100 |
| Feed composition | Lactic acid: 0.08 |
| (mole fraction) | Water vapor: 0.77 |
|  | Helium: 0.15 |
| Catalyst weight (g) | 2.0–6.0 |
| Catalyst bed height (cm) | 2.5–7.6 |
| Residence time (sec) | 0.3–5.0 |

Results of reactions over supported phosphate salts were obtained at different combinations of temperature and residence time. Residence time, calculated from actual feed rates and bed height, was the actual contact time of reactants with the catalyst. All experiments were conducted at 0.5 MPa absolute pressure using the feed composition given in Table 1.

Reaction studies were initially conducted to characterize thermal decomposition of lactic acid in the empty, quartz-lined reactor and over the Si/Al support. Representative results of experiments at 300° and 350° C. (residence time=0.3 sec) are given in Table 2.

TABLE 2

Product Yields and Selectivities[a] from Lactic Acid[b]

| | 300° C. | | | | | 350° C. | | | | |
|---|---|---|---|---|---|---|---|---|---|---|
| Temperature Substrate | None (empty reactor) | Support only | NaH$_2$PO$_4$ | Na$_2$HPO$_4$ | Na$_3$PO$_4$ | None (empty reactor) | Support only | NaH$_2$PO$_4$ | Na$_2$HPO$_4$ | Na$_3$PO$_4$ |
| Acrylic acid | 0(0) | 0.1(1) | 0.1(6) | 0.6(17) | 2.0(14) | 0.1(3) | 0.8(4) | 1.5(17) | 9.7(29) | 9.8(31) |
| 2,3-Pentanedione | 0(0) | 0.2(3) | 0.2(11) | 1.6(44) | 4.3(31) | 0(0) | 0.3(2) | 1.3(15) | 8.1(24) | 7.0(22) |
| Acetaldehyde | 0.1(20) | 1.5(22) | 0.4(22) | 0.7(19) | 1.9(14) | 1.5(43) | 9.0(48) | 2.5(28) | 6.2(19) | 5.2(16) |
| Propanoic acid | 0.1(20) | 0.5(7) | 0.1(6) | 0.2(6) | 0.9(6) | 1.3(37) | 1.2(6) | 1.7(20) | 2.7(8) | 1.5(5) |
| Hydroxyacetone | 0 | 0.1(1) | 0.1(6) | 0.1(3) | 0.6(4) | 0 | 0.4(2) | 0.4(5) | 3.3(10) | 2.9(9) |
| Other | 0.5(60) | 4.3(64) | 0.9(50) | 0.4(11) | 4.2(30) | 0.6(17) | 7.2(38) | 1.3(15) | 3.4(10) | 5.2(16) |
| CO | 0 | 0.1 | 0.4 | 0.3 | 0.6 | 1.0 | 10.6 | 1.6 | 2.1 | 3.0 |
| CO$_2$ | 0.4 | 0.2 | 0.2 | 0.9 | 5.0 | 2.6 | 1.9 | 2.1 | 9.7 | 10.2 |
| Lactic conversion (based on lactic acid recovered) | −8.4 | 5.7 | −2.5 | 5.5 | 19.9 | 1.7 | 17.4 | 17.6 | 45.5 | 39.9 |
| Lactic conversion based on product recovered) | 0.7 | 6.5 | 1.8 | 3.4 | 14.1 | 4.2 | 18.6 | 8.7 | 33.4 | 32.6 |
| Carbon recovery (%) | 109.1 | 100.8 | 104.3 | 97.8 | 94.2 | 102.4 | 101.2 | 91.1 | 87.9 | 92.7 |

[a]Selectivity given in parentheses.
[b]0.3-sec residence time

In the empty reactor, lactic acid conversion was less than 10% at 350° C. and conversion over Si/Al support gives acetaldehyde as the dominant product.

The enhancement of acrylic acid and 2,3-pentanedione yields in the presence of disodium and trisodium phosphates was clearly demonstrated in Table 2. At 300° C., the trisodium salt showed a higher overall activity, but selectivities to various products were similar within experimental uncertainty for the two salts. At 350° C., both selectivities and overall activities were similar for di- and tribasic sodium phosphates. The monosodium salt exhibited little catalytic activity at either temperature. There is a fairly good (within ±20%) correlation between combined acetaldehyde and 2,3-pentanedione yields and combined CO and CO$_2$ yields, indicating that lactic acid is primarily reacting by the pathways given in FIG. 1.

Results in Table 2 show that the primary pathway of lactic acid decomposition over the acidic silica-alumina support is decarbonylation to acetaldehyde and CO. When phosphate salts are loaded onto the support, this pathway is strongly inhibited and the smaller amount of acetaldehyde formed is mainly via decarboxylation (to give CO$_2$).

As can be seen from prior art Example 1, lactic acid is converted to acrylic acid, 2,3-pentanedione, and acetaldehyde over supported sodium phosphate salts at 0.5 MPa and 280°–350° C. Formation of 2,3-pentanedione is favored at low temperatures (280°–320° C.) and longer residence times, while acrylic acid is favored at higher temperatures (350° C.) and shorter residence times. Yields and selectivities of 2,3-pentanedione and acrylic acid reported here are not optimal, because initial studies have been conducted at relatively low lactic acid conversions to avoid secondary reactions.

EXAMPLE 2

This Example is based upon Gunter et al., Ind. Eng. Chem. 34 974–980 (1995) by some of the inventors herein.

Feedstock. Two sources of lactic acid were used in these studies. DL-Lactic acid (Aldrich, 85% aqueous solution) and L-(−)-lactic acid (Purac, Inc., Lincolnshire, Ill. 88% aqueous solution) were diluted to 34 wt % with HPLC grade water.

Supports and Catalysts. Several carbons with different pore structures were chosen for investigation as potential catalyst supports. Two gas chromatography column packings, Carbograph I and Carbograph II (Alltech, Inc., Deerfield, Ill.), were chosen as high purity, low-porosity materials. Their respective surface areas of 80 and 10 m$^2$/g (N$_2$ BET) indicate that little microporosity is present. A granular coal-based activated carbon (Strem, 10×16 mesh) with an N$_2$ BET area of 1000 m$^2$/g was used as a representative microporous carbon. This activated carbon was outgassed for 1 hour at 800° C. in N$_2$ prior to use. Finally, a biomass-based char (N$_2$ BET area 80 m$^2$/g), made by pyrolysis of cherry stones at 800° C. for 30 min in N$_2$, was tested. Ultimate analysis of this char showed low heteroatom (H,N,S) content and 4 wt % ash.

Several silica-based materials were also investigated as potential supports, ranging from nonporous Pyrex glass beads (1.0 mm diameter) to silica gel (300 m$^2$/g). Silica-alumina support (93% SiO$_2$, 7% Al$_2$O$_3$, (Johnson Matthey, Inc., Ward Hill, Mass.), hereafter referred to as Si/Al, was obtained as 2.3 mm×2.3 mm extrudate and crushed to −10+16 mesh prior to use. The Si/Al support had a BET area of 5 m$^2$/g. A series of three high-purity silica chromatographic packings (Analabs, Inc., Norwood, Mass.) was used to investigate the effect of silica pore structure on reactivity. These three silicas, denoted as XOA 400, XOB 030, and XOC 005, had BET surface areas of 400, 31, and 14 m$^2$/g, respectively, and ranged from substantially microporous (XOA 400) to macroporous (XOC 005).

All sodium salt catalysts (Aldrich) were reagent-grade chemicals in crystalline form. The following sodium salts were used: (tetra)borate (Na$_2$B$_4$O$_7$), carbonate (Na$_2$CO$_3$), (meta) silicate (Na$_2$SiO$_3$), nitrate (NaNO$_3$), phosphate (Na$_3$PO$_4$), dibasic arsenate (Na$_2$HAsO$_4$), sulfate (Na$_2$SO$_4$), chlorate (NaClO$_3$), bromate (NaBrO$_3$), and molybdate (VI) (Na$_2$MoO$_4$). Each catalyst salt was dissolved in water in the desired concentration, and catalyst support was added; complete wetting of the support was evidenced by expulsion of air upon immersion. The slurry was then heated on a hotplate with occasional stirring to boil off the water, and then dried overnight in an oven at about 100° C. Catalyst loading was 1.0 mmol of salt/g of support for all catalysts.

Apparatus and Experimental Conditions. All reactions were performed in a down-flow, quartz-lined fixed-bed reactor described in Example 1 and shown in FIG. 2 and 2A.

A typical experiment involved the evaluation of fresh catalyst at a fixed feed flow rate and four different temperatures (280°, 300°, 320°, 350° C.). Following loading, the catalyst was purged with helium while the temperature was raised to 280° C., whereupon flow of lactic acid solution was started. After product flow and the desired steady-state temperature were established, the collection of liquid products in the ice trap and gas products in a gas bag was carried out for a long enough time period to collect 2-7 mL of liquid product (40-90 min). The temperature was then changed and the product collection repeated once the new steady state was achieved. Typically, temperatures were incremented in ascending order from 280° to 350° C.; changing this order did not affect the product distribution at each temperature.

All reactions in this Example were carried out at 0.5 MPa absolute pressure at one of two feed flow rates: 0.05 mL/min lactic acid solution with 10 mL/min helium carrier or 0.1 mL/min lactic acid solution with 20 mL/min helium. These flow rates give normal contact times of reactants with the catalyst bed of 6 and 3 s, respectively.

Product Analysis. Both liquid and gas product compositions were evaluated via gas chromatography. Liquid product analysis was conducted on a Varian 3700 GC with FID detection and a glass 2 mm×2 m 4% Carbowax 20M, 80/120 Carbopack B-DA packed column (Supelco, Bellefonte, Pa.). Crude liquid reaction products were fitted with disposable syringe filters to remove minor amounts of particulates and then mixed in a 1:1 volumetric ratio with a standard solution containing 2-propanol as an internal calibration standard and oxalic acid as a column conditioner. Samples (1 µL) of the mixture were injected, and the syringe was left in the injection port (200° C.) for 1 min following injection to ensure complete sample vaporization. Response factors were determined by injecting calibration solutions with known concentrations of major products and lactic acid. Major liquid products analyzed included acetaldehyde, hydroxyacetone (acetol), 2,3-pentanedione, propanoic acid, acrylic acid, and lactic acid; minor products included ethanol, acetone, methyl acetate, acetic acid, and 2-butanone. These minor products are lumped with several unknown compounds which appear in small quantities in the liquid products; together these are reported as "other and unknown" in the results.

Gas samples were analyzed using a Stainless Steel ⅛ in.×5 ft 80/100 Carbosieve SII column (Supelco, Bellefonte, Pa.) in a Varian 3300/GC equipped with thermal conductivity detection. Carbon monoxide and carbon dioxide were the only gas products observed in these studies; their concentrations were determined by comparison of peak areas with those of a mixed calibration standard.

Product yields and selectivities from lactic acid conversion were determined for a number of supports and catalyst-support combinations at different temperatures and flow rates.

Carbon Supports. Results of lactic acid conversion over several carbons at 300° and 350° C. are given in Tables 3 and 4, respectively.

TABLE 3

Product Yields (Selectivities) over Carbon Supports at 300° C.

| | support/catalyst (surface area[a] ($m^2/g$)) | | | | | |
|---|---|---|---|---|---|---|
| | carbograph 1 (80) | carbograph 2 (10) | biomass char (80) | biomass char with $Na_3PO_4$ 80 | activated carbon (1000) | activated carbon with $Na_3PO_4$ (1000) |
| acrylic acid | 0.4(4) | 1.1(15) | 3.0(11) | 6.7(24) | 0.9(2) | 1.5(3) |
| propanoic acid | 2.3(22) | 1.6(21) | 4.6(17) | 2.7(10) | 11.8(28) | 24.7(44) |
| 2,3-pentanedione | 0.1(1) | 0.1(1) | 7.9(29) | 6.9(25) | 0.7(2) | 0.2(1) |
| acetaldehyde | 6.6(64) | 3.2(42) | 4.1(15) | 4.3(16) | 19.4(46) | 14.8(27) |
| hydroxyacetone | 0(0) | 0(0) | 2.5(9) | 4.0(14) | 0(0) | 0.4(1) |
| other + unknown | 0.9(9) | 0.4(5) | 4.7(18) | 13.1(47) | 9.2(22) | 14.2(25) |
| CO | 19.7 | 4.1 | 1.0 | 1.4 | 30.6 | 22.5 |
| $CO_2$ | 7.3 | 3.4 | 19.2 | 25.8 | 23.0 | 37.1 |
| conversion (BOF)[b] | 13.2 | 15.0 | 39.5 | 63.7 | 84.2 | 75.3 |
| conversion (BOP)[b] | 10.3 | 7.5 | 26.8 | 27.7 | 42.0 | 55.8 |
| carbon recovery (%) | 103.8 | 92.6 | 90.7 | 80.1 | 66.5 | 93.1 |

[a]$N_2$ BET at 78K.
[b]BOF - Based on lactic acid fed to reactor.
BOP - Based on total product recovery.
BOC - Based on lactic acid converted in reactor. (Table 7)

TABLE 4

Product Yields (Selectivities) over Carbon Supports at 350° C.

| | support/catalyst (surface area[a] ($m^2/g$)) | | | | | |
|---|---|---|---|---|---|---|
| | carbograph 1 (80) | carbograph 2 (10) | biomass char (80) | biomass char with $Na_3PO_4$ 80 | activated carbon (1000) | activated carbon with $Na_3PO_4$ (1000) |
| acrylic acid | 0.9(3) | 9/9(2) | 3.9(9) | 9.6(22) | 0.4(2) | 0.3(1) |
| propanoic acid | 8.4(26) | 11.4(27) | 14.1(33) | 10.8(25) | 17.1(30) | 26.2(46) |
| 2,3-pentanedione | 0.4(1) | 0.7(2) | 2.8(7) | 3.6(8) | 0.3(1) | 0.3(1) |

TABLE 4-continued

Product Yields (Selectivities) over Carbon Supports at 350° C.

| | support/catalyst (surface area*(m²/g)) | | | | | |
|---|---|---|---|---|---|---|
| | carbograph 1 (80) | carbograph 2 (10) | biomass char (80) | biomass char with Na₃PO₄ 80 | activated carbon (1000) | activated carbon with Na₃PO₄ (1000) |
| acetaldehyde | 19.4(59) | 18.4(43) | 9.2(22) | 7.3(17) | 25.0(44) | 22.6(40) |
| hydroxyacetone | 0(0) | 5.2(12) | 3.1(7) | 4.6(11) | 0(0) | 0(0) |
| other + unknown | 3.7(11) | 5.7(13) | 9.2(22) | 7.3(17) | 13.8(24) | 13.7(24) |
| CO | 21.1 | 11.4 | 8.0 | 9.6 | 34.4 | 25.9 |
| CO₂ | 40.2 | 30.9 | 40.7 | 58.7 | 31.4 | 44.8 |
| conversion (BOF)[b] | 72.1 | 56.0 | 92.6 | 92.4 | 93.9 | 95.9 |
| conversion (BOP)[b] | 32.8 | 42.3 | 42.3 | 43.2 | 56.6 | 63.1 |
| carbon recovery (%) | 74.1 | 93.1 | 60.8 | 69.7 | 71.5 | 79.3 |

*$N_2$ BET at 78K
[b]- See Table 3 for definitions.

The reactor pressure was 0.5 MPa, and the contact time was approximately 6 s for studies over carbons. Propanoic acid and acetaldehyde are the major reaction products, and lactic acid conversion generally increases with increasing carbon surface area (microporosity). Acetaldehyde and propanoic acid selectivities were similar over the Carbograph and activated carbon supports; combined selectivity to acetaldehyde and propanoic acid exceeds 70% in most cases. The carbon derived from cherry stone gave results significantly different than those on other carbons in that 2,3-pentanedione and acrylic acid were formed in significant yields. It appears that the ash, composed largely of carbonate and silicate, is primarily responsible for formation of 2,3-pentanedione and acrylic acid. The ratio of $CO_2$:CO is much greater over the cherry stone-derived carbon than over the other carbons. Even though some desirable products are formed, the wide product distribution does not make the cherry-derived carbon significantly more attractive as a catalyst support than the Carbograph carbon; its catalytic properties were therefore not pursued further.

Addition of $Na_3PO_4$ to the carbon supports had little effect on product distribution or overall activity, even though the catalyst dispersed well on the carbon supports. This indicates that the direct interaction of lactic acid with carbon dominates this catalyst and that $Na_3PO_4$ has little influence.

The data suggest that propanoic acid is formed upon direct interaction of lactic acid with carbon, as opposed to being a secondary product of acrylic acid hydrogenation.

The low acrylic acid yields over every carbon make it extremely unlikely that acrylic acid is the precursor to propanoic acid, even though high $CO_2$ yields suggest that there may be substantial $H_2$ present in the reacting gas mixture from decarboxylation of lactic acid (FIG. 1) and possibly from the water-gas shift reaction. Further, the high purity Carbograph supports do not likely have enough metal impurities present to act as efficient hydrogenation catalyst. Propanoic acid is therefore most likely formed via reduction of lactic acid by carbon. Carbon is a powerful reducing agent, but no prior observations of lactic acid-carbon interactions were found in the literature.

The combined CO and $CO_2$ yields for all experiments far exceed the values expected from the primary reaction pathways in FIG. 1. Also, the overall carbon balance is relatively poor in most experiments, especially at high temperatures. These data together suggest that substantial cracking of lactic acid is taking place in the pores of the carbon support. Some CO and $CO_2$ may be forming from the support carbon during reaction with lactic acid; this would explain the unusually high CO and $CO_2$ yields. Moderate gain in carbon support weight (5–10%) was observed over the course of reaction, indicating that products or feed are decomposing on the support.

Silica-Based Supports. Complete results of lactic acid conversion over several silica supports at 300° C., 0.5 MPa total pressure, and ~6 s contact time are given in Table 5.

TABLE 5

Product Yields (Selectivities) over Silica-Based Supports at 300° C.

| | support (surface area*(m²/g)) | | | | | |
|---|---|---|---|---|---|---|
| | Pyrex beads (<1) | silica XOC 005 (14) | silica XOB 030 (31) | silica XOA 400 (400) | silica gel (301) | Si/Al (5) |
| acrylic acid | 0.8(16) | 9.3(5) | 1.1(6) | 0.3(1) | 0.8(3) | 0.6(4) |
| propanoic acid | 0.9(18) | 0.5(8) | 18(9) | 1.1(2) | 0.9(4) | 1.2(8) |
| 2,3-pentanedione | 1.0(20) | 0.2(3) | 0.9(5) | 0.3(1) | 0.4(2) | 0.3(2) |
| acetaldehyde | 1.1(22) | 5.1(76) | 14.2(74) | 64.8(92) | 19.9(86) | 10.2(67) |
| hydroxyacetone | 0(0) | 0(0) | 0(0) | 1.1(2) | 0(0) | 0.9(6) |
| other + unknown | 1.1(22) | 0.5(8) | 1.1(6) | 2.6(4) | 1.1(5) | 2.1(13) |
| CO | 0.5 | 3.9 | 16.7 | 79.0 | 18.5 | 7.4 |
| CO₂ | 1.8 | 1.0 | 3.4 | 7.5 | 1.1 | 1.3 |
| conversion (BOF)[b] | −0.3 | 9.6 | 33.9 | 87.5 | 33.4 | 28.9 |
| conversion (BOP)[b] | 4.9 | 6.6 | 19.1 | 70.2 | 23.1 | 15.3 |

TABLE 5-continued

Product Yields (Selectivities) over Silica-Based Supports at 300° C.

| | Pyrex beads (<1) | silica XOC 005 (14) | silica XOB 030 (31) | silica XOA 400 (400) | silica gel (301) | Si/Al (5) |
|---|---|---|---|---|---|---|
| | | | support (surface area[a]($m^2/g$)) | | | |
| carbon recovery (%) | 105.5 | 97.0 | 86.9 | 89.2 | 89.3 | 85.5 |

[a] $N_2$ BET at 78 K.
[b] See Table 3 for definitions

The primary product over the silica supports is acetaldehyde, and the same general trend in conversion with support surface area observed on carbon supports is also seen on silica-based materials. This is clearly illustrated for the XO-silica supports; these chemically identical chromatographic packings differ only in pore structure. Selectivity to acetaldehyde is similar for the three XO-silicas but lactic acid conversion increases strongly with increasing support surface area. The CO and $CO_2$ yields over silica supports follow the yields of other products, indicating that reaction pathways in FIG. 1 are being followed. Decarbonylation is clearly the primary route of acetaldehyde formation. Following reaction, the silica supports had only a light brown color (as opposed to white initially), and very little weight gain (~5%) of the support was recorded. This indicates little cracking of lactic acid or products to carbon on the silica support.

Figure 4:
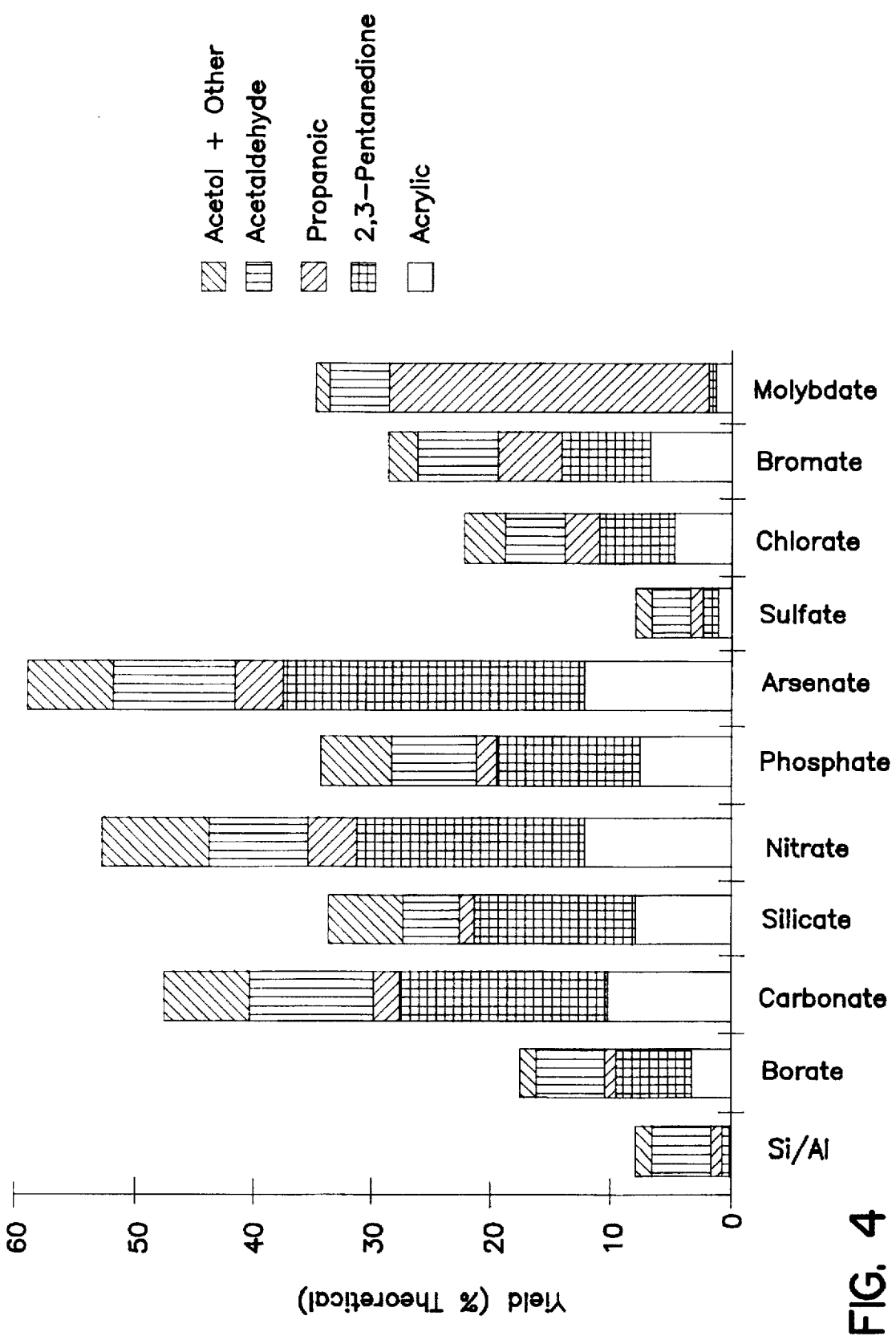
FIG. 4 is a graph showing the results of sodium salts supported on a silica-alumina support (SiAl).

Survey of Catalysts on Si/Al. Representative results of a survey of sodium salt catalysts supported on Si/Al are given in FIG. 4. These product yields were determined at 300° C., 0.5 MPa pressure, and 3 s contact time. Catalysts in group IV and group V are seen to be the best catalysts for 2,3-pentanedione and acrylic acid formation, with silicate and arsenate giving the best yield and selectivity to the diketone. Sulfate, chlorate, and bromate are all less active and less selective as catalysts, with sulfate having essentially no catalytic activity.

The results over molybdate catalyst are entirely different from those over other catalysts: propanoic acid is the dominant product and is produced at 85% selectivity. Large quantities of $CO_2$ were also produced over $Na_2MoO_4$. It is clear that molybdate is reducing lactic acid directly to propanoic acid; this is interesting because molybdenum is already in its highest oxidation state (VI) and is not expected to be an effective reducing agent. Although molybdate has interesting possibilities and potential applications as a catalyst for propanoic acid formation, the low pentanedione and acrylic acid yields make it an oddity in the context of this work.

Group V Catalysts Supported on XOC 005 Silica. Complete results of lactic acid conversion studies over group V oxide salt catalysts supported on XOC 005 and Si/Al at 300° C., 0.5 MPa total pressure, and 3 s contact time are given in Table 6.

TABLE 6

Product Yields (Selectivities) over Catalysts/Support Combinations at 300° C.

| Catalyst Support | empty reactor | XOC 005 | Si/Al | NaOH XOC 005 | NaNO₃ XOC 005 | NaNO₃ Si/Al | Na₃PO₄ XOC 005 | Na₃PO₄ Si/Al | Na₂HAsO₄ XOC 005 | Na₂HAsO₄ Si/Al |
|---|---|---|---|---|---|---|---|---|---|---|
| acrylic acid | 0.1(4) | 0.2(10) | 0.2(2) | 1.6(22) | 5.6(21) | 10.9(2.0) | 4.1(17) | 7.3(20) | 6.4(17) | 11.8(18) |
| propanoic acid | 0.8(33) | 0.4(18) | 0.7(6) | 0.9(12) | 0.8(3) | 3.7(7) | 1.4(6) | 1.7(5) | 1.2(3) | 4.0(6) |
| 2,3-pentanedione | 0.1(3) | 0.2(7) | 0.1(1) | 3.7(50) | 11.6(44) | 17.3(32) | 8.0(34) | 11.3(33) | 24.7(66) | 25.3(39) |
| acetaldehyde | 1.6(60) | 1.1(46) | 4.9(42) | 1.2(16) | 4.0(15) | 7.6(14) | 3.3(14) | 7.1(20) | 2.8(7) | 10.4(16) |
| hydroxyacetone | 0(0) | 0(0) | 0.3(3) | 0(0) | 3.1(12) | 6.3(11) | 2.0(9) | 3.9(11) | 1.0(3) | 3.8(6) |
| other + unknown | 0(0) | 0.4(19) | 5.5(46) | 0(0) | 1.5(6) | 7.7(14) | 4.8(20) | 4.1(20) | 1.6(4) | 9.6(15) |
| CO | 2.0 | 1.4 | 5.0 | 1.1 | 1.9 | 2.1 | 1.6 | 4.2 | 1.9 | 2.3 |
| CO₂ | 3.8 | 0.8 | 0.7 | 3.9 | 13.0 | 9.3 | 8.5 | 17.6 | 17.8 | 14.1 |
| conversion (BOF)[a] | −2.3 | −7.0 | 36.3 | 16.3 | 34.2 | 61.4 | 41.7 | 58.2 | 40.8 | 80.1 |
| conversion (BOP)[a] | 2.6 | 2.3 | 11.7 | 7.4 | 26.6 | 53.5 | 23.6 | 35.8 | 37.6 | 64.9 |
| carbon recovery (%) | 106.3 | 109.5 | 73.7 | 91.6 | 94.0 | 90.0 | 82.6 | 80.0 | 98.0 | 81.9 |

[a] See Table 3 for definitions.

Reactions in the empty reactor and over the support show only low conversion with acetaldehyde as the primary product. Introduction of NaOH to XOC 005 results in significant 2,3-pentanedione and acrylic acid yields, although lactic acid conversion over NaOH is relatively low. Adding group V sodium salts to the supports results in 2,3-pentanedione and acrylic acid as major products. Over $Na_2HAsO_4$, 2,3-pentanedione yield is 25%, and more significantly, the combined selectivity to desired products (acrylic acid+pentanedione) is 83% for the $Na_2HAsO_4$/XOC 005 combination.

Relative yields of CO and $CO_2$ are altered by addition of NaOH or group V catalysts. On the supports alone, CO is the dominant gas product. Addition of catalyst actually decreases CO yield and leads to greatly enhanced $CO_2$ yield. Clearly the decarbonylation pathway is inhibited by the introduction of catalyst. Overall acetaldehyde yield decreases upon addition of catalysts, but the mechanism of acetaldehyde formation shifts from decarbonylation to decarboxylation. Also, because the overall conversion is so much higher in the presence of catalyst, selectivity to acetaldehyde is lower.

Carbon mass balances were generally better over XOC 005 supported catalysts than over Si/Al supported catalysts, and XOC 005 supported catalysts had a lighter color indicating less carbon deposition than on the Si/Al supported catalysts. Significant weight gain of all catalysts was also recorded over the course of experiments, with as much as a 50% increase in weight noted in some cases. The overall higher activity of these catalysts is primarily responsible for the added carbon deposition recorded.

Figure 5A:
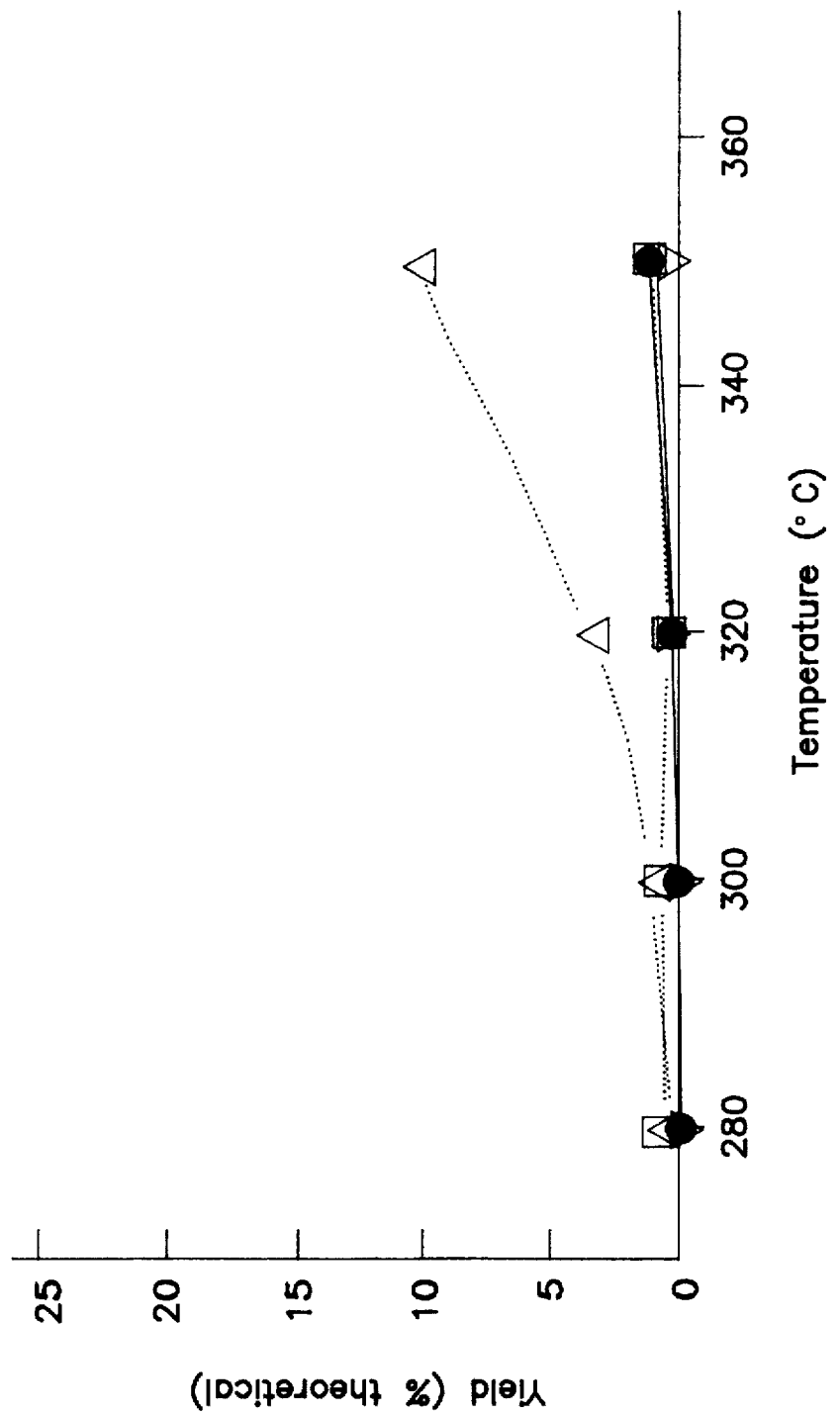
FIGS. 5A to 5E are graphs showing product yields (% of theoretical) over catalysts supported on XOC 005 silica at 3 s contact time.
Figure 5B:
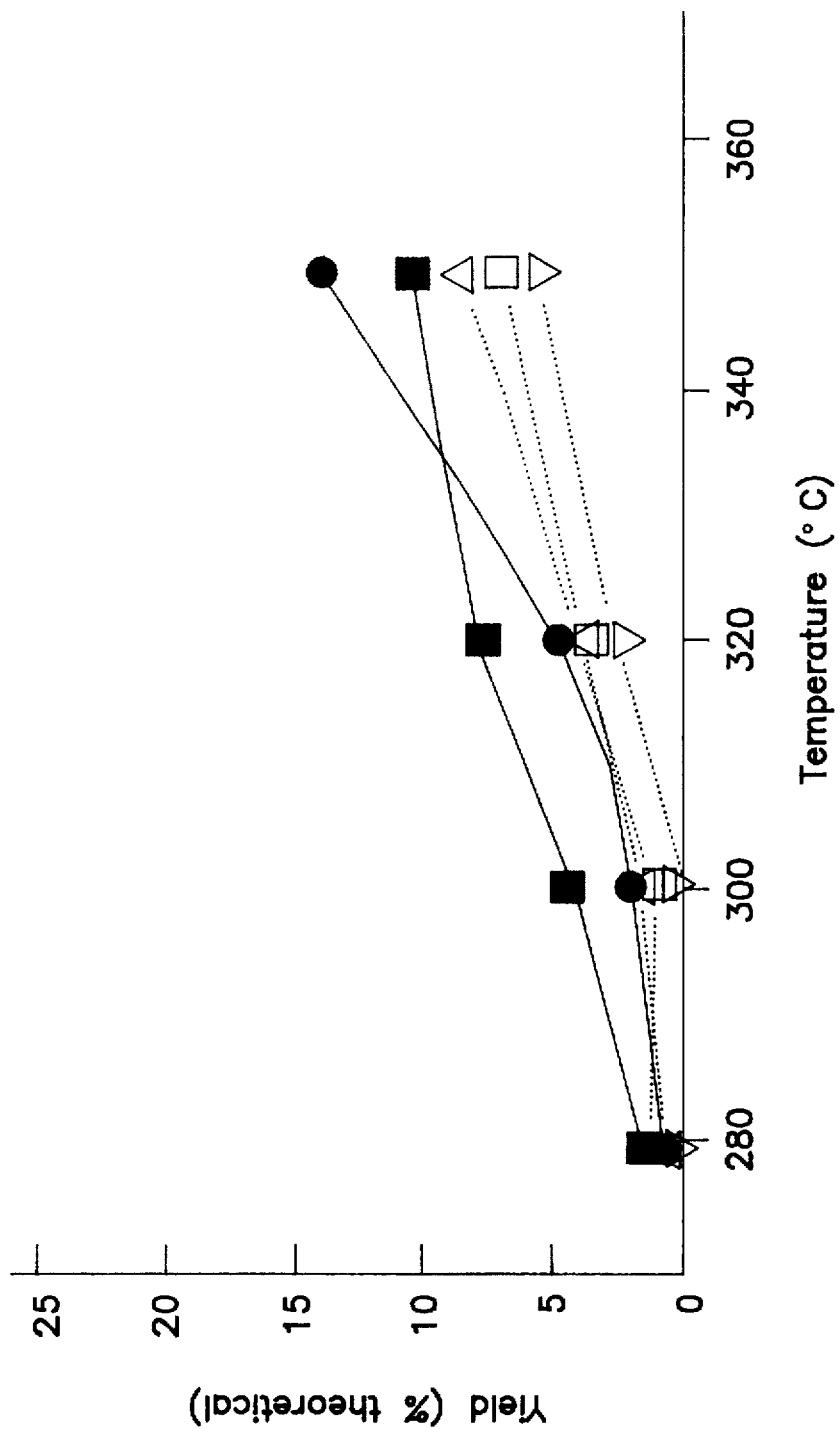
Figure 5C:
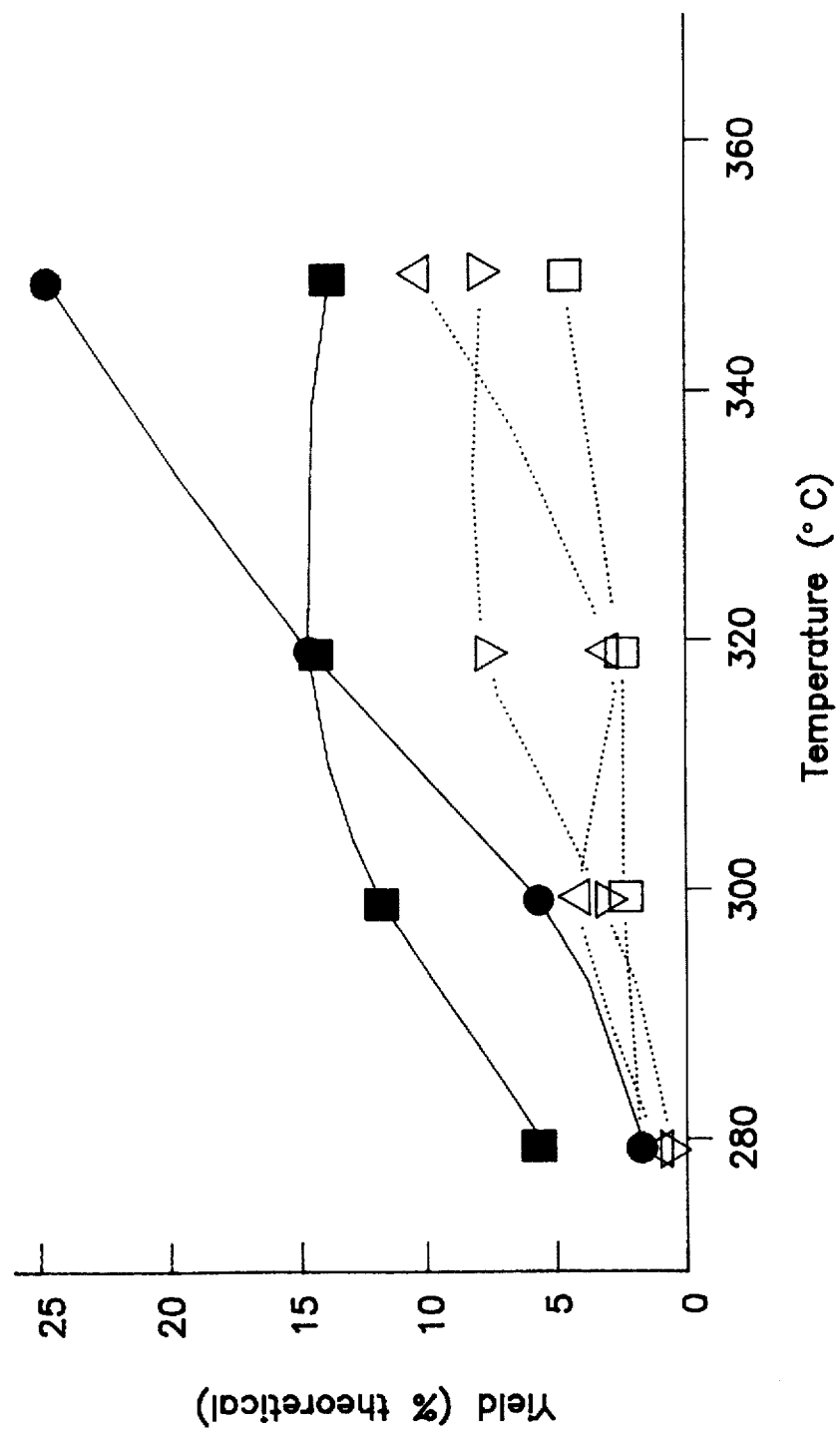
Figure 5D:
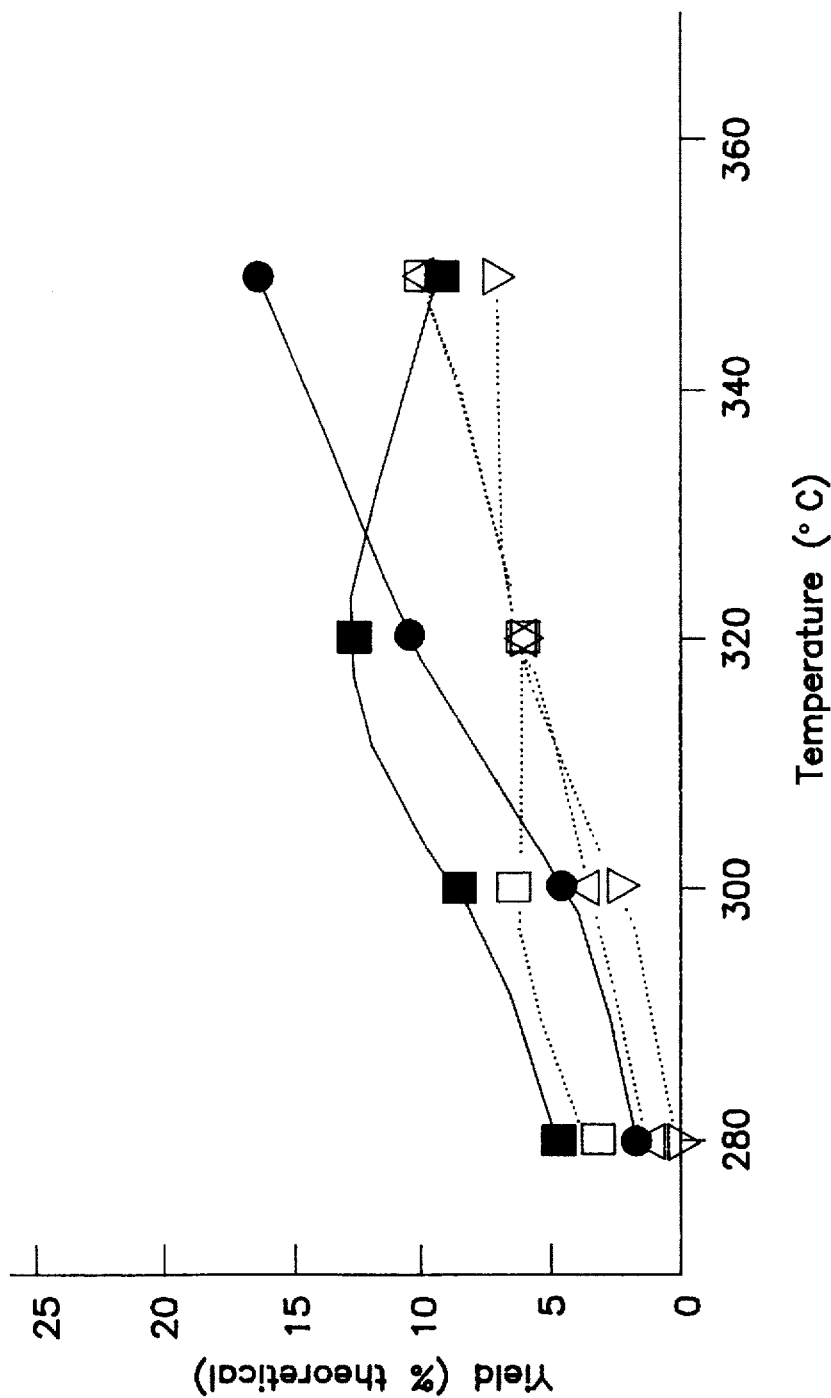
Figure 5E:
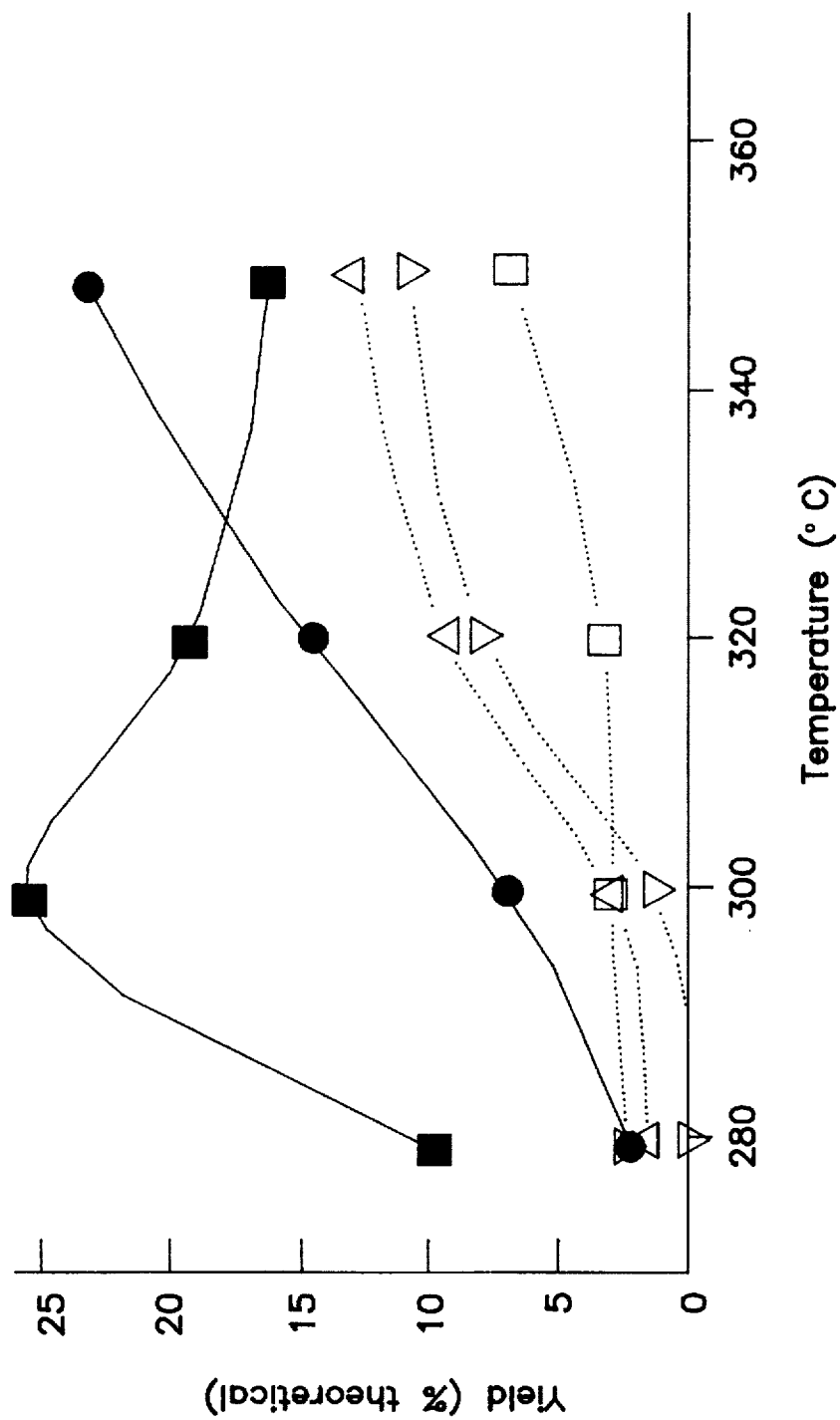

Primary product yields at different temperatures are given in FIGS. 5A to 5E for the XOC 005 support and catalysts on that support at 3 seconds reaction time. (FIG. 5A) XOC 005 support only, (FIG. 5B) NaOH, (FIG. 5C) NaNO$_3$, (FIG. 5D) Na$_3$PO$_4$, and (FIG. 5E) NaHAsO$_4$. (●) acrylic acid; (■) 2,3-pentanedione; (△) acetaldehyde; (▽) hydroxyacetone; (□) other. In these Figures, "other" products include propanoic acid as well as "other+unknown" as defined previously. As seen above, acetaldehyde formation predominates over the support alone (FIG. 5A); addition of NaOH leads to substantial 2,3-pentanedione and acrylic acid formation (FIG. 5B). The highest acrylic acid yields are achieved over NaNO$_3$ at 350° C., while the best pentanedione yields are over the arsenate catalyst. There is a clear maximum in 2,3-pentanedione yield for all three catalysts somewhere in the temperature range 300°–320° C. Acrylic acid yields increase monotonically up to 350° C.

Closure of the carbon mass balance is a primary check of the quality of results and is one of the challenges of working with lactic acid as a feedstock. Lactic acid vaporizes only with difficulty and dimerizes or polymerizes easily. These characteristics have led to the current reactor configuration and the use of helium as a carrier during reaction. In this Example 2, the quantity of unaccounted carbon as a percentage of that fed generally increases with increasing temperature ranging from an average of 0.2% at 280° C. to nearly 22% at 350° C. The percentage of unaccounted carbon tends to increase with lactic acid conversion and decreases with increased feed-flow rate.

The catalyst survey shows relatively weak trends in activity and selectivity to desired products with position in the periodic table. First, it appears that conversion and selectivity to 2,3-pentanedione increase as one goes down a group and that in general the more basic salts give higher 2,3-pentanedione selectivity. Thus, chlorate, bromate, and sulfate are less effective catalysts than carbonate, silicate, phosphate, and arsenate. There are exceptions, however: NaNO$_3$, a neutral salt, is a good catalyst, whereas Na$_2$SO$_4$, also neutral, is a poor catalyst. While this trend in increased 2,3-pentanedione yield with increasing basicity of the salt agrees with the results of our previous studies using Na$_{3-y}$H$_y$PO$_4$ catalysts (y=0, 1, 2), it is clear that catalyst behavior is tied to much more than salt basicity or position in the periodic table.

Several of the salts studied here are known to undergo thermal transformations to different chemical species upon heating. For instance, NaNO$_3$ gives off oxygen and forms NaNO$_2$ around 450° C., and Na$_2$HAsO$_4$ decomposes to sodium pyroarsenate (Na$_4$As$_2$O$_7$) at 180°–200° C. While transformations of most of the neat salts have been characterized, there is no certainty that these are the only changes occurring. For example, the product solution from reaction over the arsenate catalyst contained a small quantity of black powder. A solid-probe mass spectrum of this solid (obtained by filtering the product solution) gave masses at 75, 150, 225, and 300, indicating that the particles are elemental arsenic (As$_4$). A quantitative analysis was not performed to determine how much arsenate was reduced to elemental arsenic, but this finding obviously makes the arsenate less desirable as a catalyst from both an environmental and a stability standpoint.

It is speculated that the salts of Examples 1 and 2 interact with either the support or with lactic acid and undergo transformation to the species responsible for the catalytic activity. The relatively similar catalytic behavior of group IV and group V sodium salts over Si/Al supports indicates that the interaction of the support with the salt is somehow related to the catalytic behavior. This is further supported by the lack of influence of Na$_3$PO$_4$ on product distributions over carbon supports. All of the Examples 1 and 2 show relatively low yield and selectivity.

EXAMPLE 3

Figure 6:
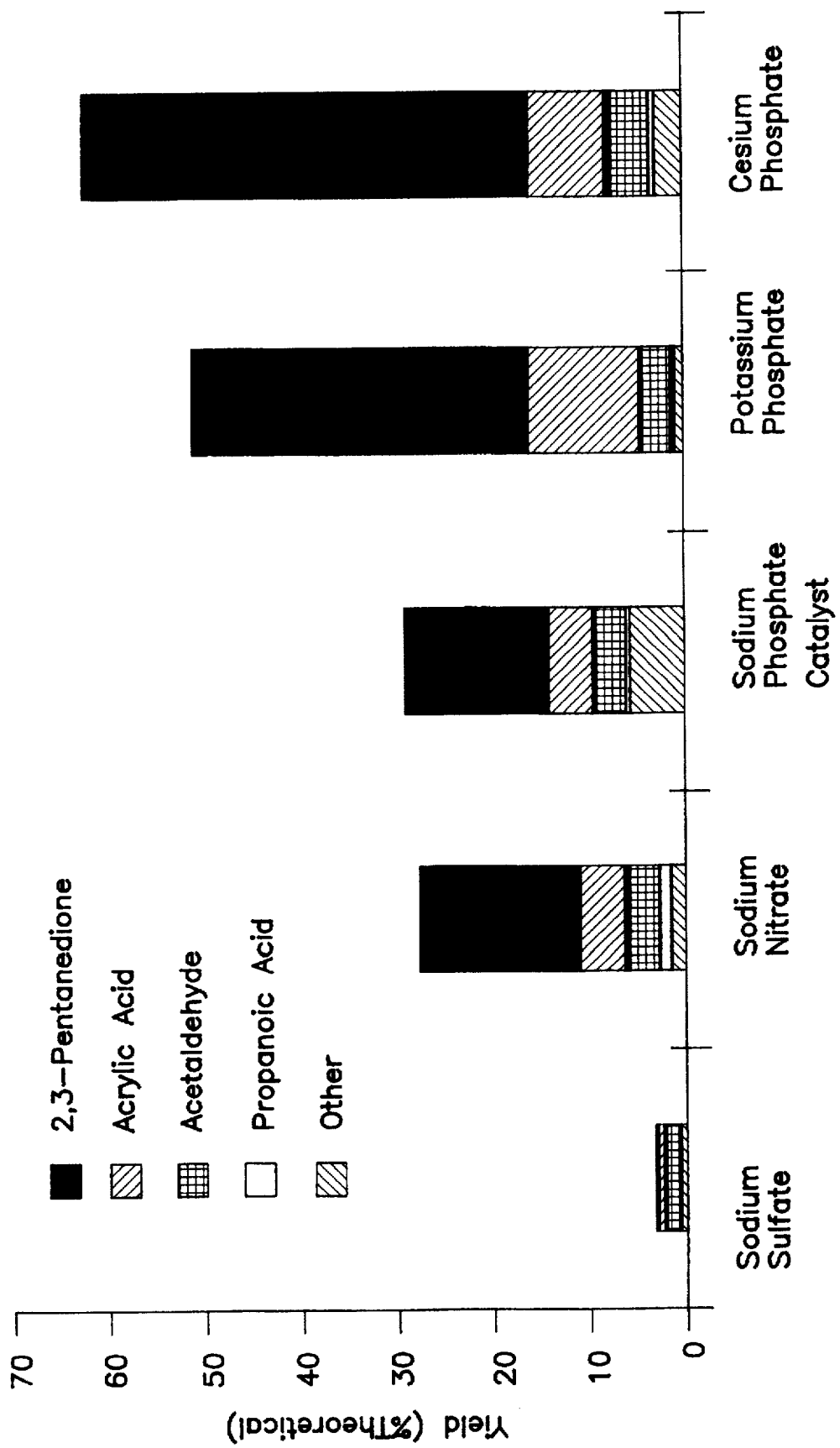
FIG. 6 is a graph showing the comparative results of the conversion with various salts wherein only the cesium and potassium phosphates produce a high yield of 2,3-pentanedione.

FIG. 6 is a graph showing the comparative results using various salts using the process as set forth in Examples 1 and 2. Further results are shown in Table 7. The pressure was 0.5 MPa. The results with certain potassium and cesium salts and bases are particularly unexpected in view of the results of Examples 1 and 2.

TABLE 7

| Cat. | CsOH:H3PO4 | CsOH:H3PO4 | CsOH:H3PO4 | CsOH:H3PO4 | CsOH:H3PO4 | CsOH:H3PO4 |
| --- | --- | --- | --- | --- | --- | --- |
| T(C) | 260.000 | 280.000 | 300.000 | 320.000 | 350.000 | 370.000 |
| RT(s) | 3.645 | 3.567 | 3.488 | 3.356 | 3.276 | 3.062 |
| Err(% C) | −7.569 | 2.127 | −20.492 | −30.909 | −47.905 | −41.635 |
| Conv(BOF) | 44.247 | 74.829 | 94.292 | 93.057 | 99.179 | 90.573 |
| Conv(adj) | 36.678 | 76.956 | 73.799 | 62.148 | 51.274 | 48.937 |
| Yld BOF (%) | | | | | | |
| Acryl | 3.895 | 6.881 | 1.543 | 0.000 | 0.000 | 0.000 |
| Prop | 0.836 | 0.581 | 0.646 | 1.367 | 5.614 | 9.915 |
| 23P | 25.158 | 59.707 | 50.178 | 26.967 | 14.022 | 6.283 |
| Acetal | 5.393 | 4.734 | 5.147 | 6.420 | 10.667 | 14.425 |
| Acetol | 0.000 | 0.000 | 0.000 | 0.000 | 0.000 | 0.000 |
| Oth | 0.478 | 0.439 | 0.744 | 1.376 | 2.832 | 1.138 |
| Unknown | 0.477 | 3.306 | 12.000 | 14.647 | 10.561 | 6.153 |
| Unacct | 8.010 | −0.819 | 23.433 | 42.280 | 55.482 | 52.659 |
| CO* | 3.185 | 1.563 | 0.948 | 2.781 | 3.697 | 7.332 |
| CO2* | 17.065 | 37.857 | 39.888 | 53.559 | 41.493 | 46.536 |
| Yld BOC (%) | | | | | | |

TABLE 7-continued

| | | | | | | |
|---|---|---|---|---|---|---|
| Acryl | 8.803 | 9.195 | 1.637 | 0.000 | 0.000 | 0.000 |
| Prop | 1.890 | 0.777 | 0.686 | 1.469 | 5.661 | 10.947 |
| 23P | 56.858 | 79.791 | 53.216 | 28.979 | 14.138 | 6.937 |
| Acetal | 12.188 | 6.327 | 6.095 | 6.899 | 10.755 | 15.927 |
| Acetol | 0.000 | 0.000 | 0.000 | 0.000 | 0.000 | 0.000 |
| Oth | 1.081 | 0.587 | 0.789 | 1.479 | 2.856 | 1.257 |
| Unknown | 1.078 | 4.418 | 12.726 | 15.740 | 10.648 | 6.793 |
| Unacct | 18.103 | −1.094 | 24.852 | 45.435 | 55.942 | 58.139 |
| CO* | 7.199 | 2.088 | 1.005 | 2.988 | 3.728 | 8.095 |
| CO2* | 38.568 | 50.591 | 42.303 | 51.556 | 41.837 | 51.379 |
| Sel (%) | | | | | | |
| Acryl | 10.892 | 9.511 | 2.622 | 0.000 | 0.000 | 0.000 |
| Prop | 2.338 | 0.893 | 1.098 | 3.783 | 16.944 | 31.216 |
| 23P | 70.352 | 82.534 | 85.252 | 74.640 | 42.316 | 19.783 |
| Acetal | 15.081 | 6.544 | 9.765 | 17.769 | 32.192 | 45.417 |
| Acetol | 0.000 | 0.000 | 0.000 | 0.000 | 0.000 | 0.000 |
| Oth | 1.337 | 0.607 | 1.264 | 3.808 | 8.548 | 3.583 |
| Cat. | CsOH/H3PO4 | CsOH/H3PO4 | CsOH/H3PO4 | CsOH/H3PO4 | CsOH/H3PO4 | CsOH/H3PO4 |
| T(C) | 260.000 | 280.000 | 300.000 | 320.000 | 350.000 | 370.000 |
| RT(s) | 3.884 | 3.651 | 3.636 | 3.549 | 3.114 | 3.089 |
| Err(% C) | −1.975 | −4.784 | −33.708 | −46.564 | −44.660 | −50.077 |
| Conv(BOF) | 34.640 | 71.362 | 97.729 | 97.973 | 97.141 | 96.734 |
| Conv(adj) | 32.665 | 66.579 | 64.021 | 51.409 | 52.481 | 46.657 |
| Yld BOF (%) | | | | | | |
| Acryl | 4.236 | 7.668 | 5.515 | 1.253 | 0.000 | 0.000 |
| Prop | 0.592 | 0.412 | 0.496 | 0.586 | 1.085 | 1.854 |
| 23P | 22.491 | 47.357 | 40.074 | 30.462 | 21.263 | 15.049 |
| Acetal | 3.026 | 4.293 | 5.498 | 5.109 | 6.270 | 8.904 |
| Acetol | 0.000 | 1.353 | 1.129 | 0.000 | 0.000 | 0.000 |
| Oth | 0.681 | 0.585 | 0.604 | 1.015 | 3.260 | 4.248 |
| Unknown | 0.335 | 1.264 | 5.217 | 7.815 | 8.318 | 8.125 |
| Unacct | 3.279 | 8.431 | 39.195 | 51.733 | 56.945 | 58.554 |
| CO* | 2.641 | 1.476 | 1.612 | 1.684 | 3.555 | 4.930 |
| CO2* | 16.559 | 38.386 | 41.550 | 35.806 | 55.461 | 43.517 |
| Yld BOC (%) | | | | | | |
| Acryl | 12.229 | 10.746 | 5.643 | 1.278 | 0.000 | 0.000 |
| Prop | 1.708 | 0.577 | 0.508 | 0.599 | 1.117 | 1.916 |
| 23P | 64.927 | 66.361 | 41.005 | 31.092 | 21.889 | 15.557 |
| Acetal | 8.735 | 6.016 | 5.626 | 5.215 | 6.455 | 9.204 |
| Acetol | 0.000 | 1.896 | 1.156 | 0.000 | 0.000 | 0.000 |
| Oth | 1.967 | 0.819 | 0.618 | 1.035 | 3.356 | 4.391 |
| Unknown | 0.968 | 1.771 | 5.338 | 7.977 | 8.563 | 8.400 |
| Unacct | 9.467 | 11.814 | 40.106 | 52.803 | 58.621 | 60.531 |
| CO* | 7.624 | 2.069 | 1.650 | 1.719 | 3.660 | 5.096 |
| CO2* | 47.802 | 53.791 | 42.516 | 36.546 | 57.093 | 44.986 |
| Sel (%) | | | | | | |
| Acryl | 13.653 | 12.435 | 10.344 | 3.260 | 0.000 | 0.000 |
| Prop | 1.907 | 0.668 | 0.931 | 1.526 | 3.404 | 6.168 |
| 23P | 72.491 | 76.794 | 75.162 | 79.277 | 66.701 | 50.073 |
| Acetal | 9.753 | 6.961 | 10.312 | 13.297 | 19.669 | 29.626 |
| Acetol | 0.000 | 2.194 | 2.118 | 0.000 | 0.000 | 0.000 |
| Oth | 2.196 | 0.948 | 1.133 | 2.640 | 10.227 | 14.133 |
| Cat. | CsNO3 | CsNO3 | CsNO3 | CsNO3 | CsNO3 | CsNO3 |
| T(C) | 260.000 | 280.000 | 300.000 | 320.000 | 350.000 | 370.000 |
| RT(s) | 3.418 | 3.270 | 3.339 | 3.196 | 3.127 | 3.025 |
| Err(% C) | −1.250 | −26.723 | −28.483 | −32.210 | −40.844 | −44.146 |
| Conv(BOF) | 45.281 | 100.000 | 97.827 | 96.658 | 93.796 | 94.458 |
| Conv(adj) | 44.031 | 73.277 | 69.344 | 64.448 | 52.951 | 50.312 |
| Yld BOF (%) | | | | | | |
| Acryl | 4.634 | 6.952 | 3.982 | 2.171 | 0.835 | 0.631 |
| Prop | 0.472 | 0.522 | 1.005 | 1.714 | 2.460 | 4.259 |
| 23P | 34.529 | 49.464 | 38.661 | 26.280 | 11.463 | 6.744 |
| Acetal | 2.897 | 7.506 | 10.016 | 11.124 | 11.422 | 13.729 |
| Acetol | 0.000 | 3.160 | 2.744 | 1.423 | 0.000 | 0.000 |
| Oth | 0.207 | 0.478 | 1.195 | 2.143 | 3.388 | 4.286 |
| Unknown | 1.120 | 3.667 | 7.809 | 13.864 | 14.495 | 12.867 |
| Unacct | 1.423 | 28.251 | 32.415 | 37.940 | 49.732 | 51.943 |
| CO* | 0.859 | 1.532 | 2.339 | 3.129 | 9.299 | 8.849 |
| CO2* | 20.453 | 36.400 | 41.168 | 42.041 | 40.642 | 38.943 |
| Yld BOC (%) | | | | | | |
| Acryl | 10.233 | 6.952 | 4.071 | 2.246 | 0.890 | 0.668 |
| Prop | 1.042 | 0.522 | 1.027 | 1.773 | 2.623 | 4.509 |
| 23P | 76.255 | 49.464 | 39.519 | 27.189 | 12.221 | 7.140 |
| Acetal | 6.397 | 7.506 | 10.239 | 11.509 | 12.178 | 14.534 |
| Acetol | 0.000 | 3.160 | 2.805 | 1.472 | 0.000 | 0.000 |

TABLE 7-continued

| | | | | | | |
|---|---|---|---|---|---|---|
| Oth | 0.458 | 0.478 | 1.222 | 2.217 | 3.612 | 4.537 |
| Unknown | 2.474 | 3.667 | 7.983 | 14.343 | 15.454 | 13.621 |
| Unacct | 3.142 | 28.251 | 33.136 | 39.251 | 53.021 | 54.990 |
| CO* | 1.896 | 1.532 | 2.390 | 3.237 | 9.914 | 9.368 |
| CO2* | 45.169 | 36.400 | 42.083 | 43.494 | 43.330 | 41.227 |
| Sel (%) | | | | | | |
| Acryl | 10.842 | 10.212 | 6.913 | 4.841 | 2.825 | 2.129 |
| Prop | 1.104 | 0.766 | 1.744 | 3.820 | 8.319 | 14.364 |
| 23P | 80.792 | 72.653 | 67.117 | 58.590 | 38.768 | 22.747 |
| Acetal | 6.777 | 11.025 | 17.388 | 24.800 | 38.629 | 46.305 |
| Acetol | 0.000 | 4.642 | 4.763 | 3.172 | 0.000 | 0.000 |
| Oth | 0.485 | 0.702 | 2.075 | 4.777 | 11.459 | 14.456 |

| Cat. | CsOH/CPG | CsOH/CPG | CsOH/CPG | CsOH/CPG | CsOH/CPG | CsOH/CPG |
|---|---|---|---|---|---|---|
| T(C) | 260.000 | 280.000 | 300.000 | 320.000 | 350.000 | 370.000 |
| RT(s) | 4.048 | 3.907 | 3.971 | 3.657 | 3.300 | 3.199 |
| Err(% C) | 25.657 | −13.559 | −33.570 | −46.257 | −48.912 | −52.992 |
| Conv(BOF) | 26.996 | 87.954 | 97.348 | 96.389 | 94.456 | 94.428 |
| Conv(adj) | 52.653 | 74.395 | 63.778 | 50.131 | 45.544 | 41.436 |
| Yld BOF (%) | | | | | | |
| Acryl | 3.477 | 6.089 | 2.394 | 0.594 | 0.030 | 0.000 |
| Prop | 0.000 | 2.597 | 4.885 | 3.630 | 4.535 | 5.137 |
| 23P | 41.604 | 48.712 | 36.399 | 19.056 | 8.502 | 5.057 |
| Acetal | 6.337 | 7.987 | 9.122 | 9.697 | 10.365 | 10.931 |
| Acetol | 0.000 | 4.190 | 2.540 | 0.000 | 0.000 | 0.386 |
| Oth | 0.000 | 6.716 | 1.254 | 1.807 | 2.398 | 2.977 |
| Unknown | 5.671 | 4.564 | 10.298 | 14.364 | 14.336 | 11.479 |
| Unacct | −30.093 | 7.098 | 30.456 | 47.241 | 54.291 | 58.460 |
| CO* | 2.503 | 0.995 | 1.1219 | 1.778 | 5.056 | 5.461 |
| CO2* | 12.051 | 19.172 | 19.020 | 23.280 | 30.188 | 30.188 |
| Yld BOC (%) | | | | | | |
| Acryl | 12.879 | 6.923 | 2.460 | 0.616 | 0.031 | 0.000 |
| Prop | 0.000 | 2.952 | 5.018 | 3.766 | 4.801 | 5.440 |
| 23P | 154.111 | 55.384 | 37.390 | 19.769 | 9.001 | 5.355 |
| Acetal | 23.475 | 9.081 | 9.370 | 10.060 | 10.973 | 11.576 |
| Acetol | 0.000 | 4.764 | 2.609 | 0.000 | 0.000 | 0.409 |
| Oth | 0.000 | 7.636 | 1.288 | 1.875 | 2.538 | 3.153 |
| Unknown | 21.006 | 5.189 | 10.579 | 14.902 | 15.177 | 12.157 |
| Unacct | −111.471 | 8.071 | 31.286 | 49.911 | 57.478 | 61.910 |
| CO* | 9.271 | 1.132 | 1.150 | 1.844 | 5.353 | 5.783 |
| CO2* | 44.639 | 21.798 | 19.538 | 24.152 | 31.960 | 31.969 |
| Sel (%) | | | | | | |
| Acryl | 6.762 | 7.982 | 4.231 | 1.707 | 0.115 | 0.000 |
| Prop | 0.000 | 3.403 | 8.631 | 10.437 | 17.558 | 20.978 |
| 23P | 80.913 | 63.850 | 64.316 | 54.784 | 32.916 | 20.650 |
| Acetal | 12.325 | 10.470 | 16.118 | 27.878 | 40.128 | 44.636 |
| Acetol | 0.000 | 5.492 | 4.489 | 0.000 | 0.000 | 1.578 |
| Oth | 0.000 | 8.803 | 2.215 | 5.195 | 9.283 | 12.158 |

| Cat. | KOH/K3PO4 | KOH/K3PO4 | KOH/K3PO4 | KOH/K3PO4 | KOH/K3PO4 |
|---|---|---|---|---|---|
| T(C) | 260.000 | 280.000 | 300.000 | 320.000 | 350.000 |
| RT(s) | 3.415 | 3.295 | 3.266 | 3.145 | 3.00 |
| Err(% C) | −8.049 | −29.668 | −20.923 | −35.388 | −45.248 |
| Conv(BOF) | 43.919 | 96.488 | 96.202 | 94.587 | 95.247 |
| Conv(adj) | 35.870 | 66.820 | 75.278 | 59.198 | 49.999 |
| Yld BOF (%) | | | | | |
| Acryl | 4.742 | 8.875 | 6.123 | 1.086 | 1.314 |
| Prop | 0.000 | 0.000 | 0.000 | 2.170 | 2.702 |
| 23P | 27.337 | 50.165 | 47.626 | 36.499 | 18.535 |
| Acetal | 2.840 | 4.198 | 6.022 | 5.263 | 8.169 |
| Acetol | 0.000 | 1.096 | 1.311 | 0.472 | 0.000 |
| Oth | 0.000 | 0.000 | 5.900 | 0.921 | 1.547 |
| Unknown | 0.748 | 1.827 | 5.535 | 6.385 | 5.983 |
| Unacct | 8.251 | 30.327 | 23.685 | 41.791 | 56.995 |
| CO* | 2.128 | 1.340 | 1.624 | 2.323 | 4.513 |
| CO2* | 15.286 | 30.241 | 42.790 | 41.752 | 50.440 |
| Yld BOC (%) | | | | | |
| Acryl | 10.798 | 9.198 | 6.365 | 1.148 | 1.380 |
| Prop | 0.000 | 0.000 | 0.000 | 2.294 | 2.837 |
| 23P | 62.245 | 51.991 | 49.507 | 38.588 | 19.460 |
| Acetal | 6.466 | 4.351 | 6.259 | 5.565 | 8.577 |
| Acetol | 0.000 | 1.136 | 1.362 | 0.499 | 0.000 |
| Oth | 0.000 | 0.000 | 6.133 | 0.973 | 1.625 |
| Unknown | 1.704 | 1.893 | 5.753 | 6.750 | 6.282 |
| Unacct | 18.787 | 31.431 | 24.620 | 44.182 | 59.840 |
| CO* | 4.846 | 1.389 | 1.688 | 2.456 | 4.738 |
| CO2* | 34.804 | 31.342 | 44.480 | 44.141 | 52.957 |

TABLE 7-continued

| Sel (%) | | | | | | |
|---|---|---|---|---|---|---|
| Acryl | 13.581 | 13.795 | 9.142 | 2.340 | 4.072 | |
| Prop | 0.000 | 0.000 | 0.000 | 4.676 | 8.374 | |
| 23P | 78.287 | 77.976 | 71.103 | 78.643 | 57.442 | |
| Acetal | 8.133 | 6.526 | 8.990 | 11.341 | 25.317 | |
| Acetol | 0.000 | 1.703 | 1.957 | 1.017 | 0.000 | |
| Oth | 0.000 | 0.000 | 8.809 | 1.984 | 4.795 | |

| Cat. | KOH/CPG | KOH/CPG | KOH/CPG | KOH/CPG | KOH/CPG | KOH/CPG |
|---|---|---|---|---|---|---|
| T(C) | 260.000 | 280.000 | 300.000 | 320.000 | 350.000 | 370.000 |
| RT(s) | 3.446 | 3.792 | 3.103 | 3.363 | 3.588 | 3.354 |
| Err(% C) | 6.841 | −15.617 | −12.949 | −17.075 | −28.432 | −41.742 |
| Conv(BOF) | 9.439 | 65.516 | 83.956 | 96.679 | 95.615 | 96.003 |
| Conv(adj) | 16.281 | 49.900 | 71.007 | 79.603 | 67.183 | 54.262 |
| Yld BOF (%) | | | | | | |
| Acryl | 1.993 | 6.813 | 12.544 | 13.540 | 6.100 | 4.767 |
| Prop | 0.818 | 1.956 | 2.145 | 3.910 | 5.368 | 6.142 |
| 23P | 9.741 | 33.891 | 41.578 | 39.831 | 19.789 | 12.138 |
| Acetal | 2.226 | 3.876 | 8.692 | 11.869 | 24.695 | 19.512 |
| Acetol | 0.358 | 2.912 | 6.273 | 7.620 | 3.413 | 2.657 |
| Oth | 0.000 | 0.387 | 0.582 | 1.414 | 2.189 | 1.959 |
| Unknown | 1.250 | 2.087 | 2.868 | 5.130 | 6.639 | 5.608 |
| Unacct | −6.947 | 13.594 | 9.276 | 13.364 | 27.423 | 43.220 |
| CO* | 1.339 | 1.530 | 1.274 | 2.130 | 11.521 | 9.086 |
| CO2* | 5.803 | 14.050 | 18.406 | 20.879 | 22.982 | 23.204 |
| Yld BOC (%) | | | | | | |
| Acryl | 21.133 | 10.399 | 14.941 | 14.005 | 6.380 | 4.966 |
| Prop | 8.668 | 2.986 | 2.554 | 4.045 | 5.614 | 6.398 |
| 23P | 103.201 | 51.729 | 49.523 | 41.199 | 20.697 | 12.644 |
| Acetal | 23.578 | 5.916 | 10.353 | 12.277 | 25.828 | 20.324 |
| Acetol | 3.796 | 4.445 | 7.472 | 7.882 | 3.569 | 2.768 |
| Oth | 0.000 | 0.590 | 0.693 | 1.463 | 2.289 | 2.041 |
| Unknown | 13.246 | 3.186 | 3.416 | 5.307 | 6.943 | 5.841 |
| Unacct | −73.602 | 20.749 | 11.048 | 13.823 | 28.6.81 | 45.019 |
| CO* | 14.186 | 2.335 | 1.518 | 2.203 | 12.050 | 9.464 |
| CO2* | 61.473 | 21.445 | 21.924 | 21.597 | 24.036 | 24.170 |
| Sel (%) | | | | | | |
| Acryl | 13.166 | 13.671 | 17.467 | 17.318 | 9.910 | 10.105 |
| Prop | 5.405 | 3.926 | 2.986 | 5.001 | 8.720 | 13.020 |
| 23P | 64.357 | 68.006 | 57.898 | 50.945 | 32.149 | 25.730 |
| Acetal | 14.704 | 7.777 | 12.103 | 15.181 | 40.120 | 41.359 |
| Acetol | 2.367 | 5.844 | 8.735 | 9.746 | 5.545 | 5.633 |
| Oth | 0.000 | 0.776 | 0.810 | 1.808 | 3.556 | 4.152 |

| Cat. | KNO3 | KNO3 | KNO3 | KNO3 | KNO3 | KNO3 |
|---|---|---|---|---|---|---|
| T(C) | 260.000 | 280.000 | 300.000 | 320.000 | 350.000 | 370.000 |
| RT(s) | 3.427 | 3.594 | 3.189 | 3.073 | 3.032 | 2.953 |
| Err(% C) | 11.422 | 8.455 | 2.668 | −15.491 | −27.110 | −36.345 |
| Conv(BOF) | 14.640 | 42.438 | 98.289 | 99.088 | 97.235 | 97.915 |
| Conv(adj) | 26.061 | 50.893 | 100.957 | 83.597 | 70.125 | 61.570 |
| Yld BOF (%) | | | | | | |
| Acryl | 2.966 | 8.711 | 19.116 | 9.599 | 2.657 | 0.511 |
| Prop | 0.315 | 0.293 | 0.654 | 1.254 | 3.084 | 4.620 |
| 23P | 15.052 | 33.470 | 43.157 | 40.382 | 26.620 | 16.005 |
| Acetal | 4.172 | 4.774 | 11.059 | 16.574 | 20.048 | 21.186 |
| Acetol | 0.000 | 2.330 | 8.743 | 5.987 | 1.745 | 0.168 |
| Oth | 0.789 | 0.546 | 0.804 | 1.746 | 4.136 | 4.046 |
| Unknown | 4.324 | 0.914 | 16.577 | 6.894 | 9.238 | 7.582 |
| Unacct | −12.918 | −8.600 | −1.822 | 16.652 | 29.707 | 43.798 |
| CO* | 1.637 | 1.773 | 1.770 | 2.978 | 8.227 | 17.844 |
| CO2* | 6.416 | 20.243 | 35.057 | 40.368 | 39.303 | 39.686 |
| Yld BOC (%) | | | | | | |
| Acryl | 20.259 | 20.525 | 19.449 | 9.688 | 2.732 | 0.521 |
| Prop | 2.155 | 0.691 | 0.665 | 1.265 | 3.172 | 4.718 |
| 23P | 102.814 | 78.869 | 43.909 | 40.754 | 27.377 | 16.346 |
| Acetal | 28.497 | 11.250 | 11.252 | 16.727 | 20.618 | 21.637 |
| Acetol | 0.000 | 5.491 | 8.895 | 6.043 | 1.795 | 0.172 |
| Oth | 5.387 | 1.286 | 0.818 | 1.762 | 4.254 | 4.132 |
| Unknown | 29.537 | 2.154 | 16.865 | 6.958 | 9.501 | 7.743 |
| Unacct | −88.649 | −20.266 | −1.853 | 16.805 | 30.552 | 44.731 |
| CO* | 11.181 | 4.179 | 1.801 | 3.006 | 8.461 | 18.224 |
| CO2* | 43.828 | 47.700 | 35.667 | 40.740 | 40.421 | 40.531 |
| Sel (%) | | | | | | |
| Acryl | 12.732 | 17.318 | 22.885 | 12.707 | 4.558 | 1.097 |
| Prop | 1.354 | 0.585 | 0.783 | 1.659 | 5.291 | 9.927 |
| 23P | 64.617 | 66.775 | 51.665 | 53.456 | 45.668 | 34.394 |
| Acetal | 17.910 | 9.525 | 13.239 | 21.940 | 34.394 | 45.527 |

TABLE 7-continued

| | | | | | | |
|---|---|---|---|---|---|---|
| Acetol | 0.000 | 4.649 | 10.466 | 7.926 | 2.994 | 0.362 |
| Oth | 3.386 | 1.089 | 0.963 | 2.311 | 7.096 | 8.694 |
| Cat. | K3PO4 | K3PO4 | K3PO4 | K3PO4 | K3PO4 | K3PO4 |
| T(C) | 260.000 | 280.000 | 300.000 | 320.000 | 350.000 | 370.000 |
| RT(s) | 2.897 | 2.981 | 2.804 | 2.611 | 2509 | 2.444 |
| Err(% C) | 0.912 | −7.390 | −14.220 | −12.279 | −20.031 | −35.383 |
| Conv(BOF) | 23.697 | 58.616 | 98.875 | 95.912 | 94.806 | 97.963 |
| Conv(adj) | 24.609 | 51.226 | 84.654 | 83.632 | 74.775 | 62.580 |
| Yld BOF (%) | | | | | | |
| Acryl | 4.850 | 11.899 | 16.509 | 7.691 | 1.465 | 0.603 |
| Prop | 0.337 | 0.295 | 0.480 | 0.883 | 1.803 | 1.972 |
| 23P | 16.191 | 35.082 | 52.619 | 51.053 | 35.739 | 22.889 |
| Acetal | 2.981 | 3.194 | 5.751 | 7.307 | 12.070 | 14.156 |
| Acetol | 0.000 | 0.000 | 1.913 | 1.507 | 0.000 | 0.000 |
| Oth | 0.652 | 0.212 | 0.478 | 1.268 | 3.190 | 3.667 |
| Unknown | 0.231 | 1.079 | 4.761 | 10.806 | 13.841 | 10.749 |
| Unacct | −1.544 | 6.855 | 16.363 | 15.397 | 26.699 | 43.926 |
| CO* | 1.814 | 1.325 | 1.592 | 2.696 | 6.913 | 7.951 |
| CO2* | 8.248 | 18.322 | 37.978 | 41.712 | 48.437 | 49.546 |
| Yld BOC (%) | | | | | | |
| Acryl | 20.468 | 20.300 | 16.697 | 8.019 | 1.546 | 0.616 |
| Prop | 1.421 | 0.503 | 0.486 | 0.921 | 1.901 | 2.013 |
| 23P | 68.325 | 59.851 | 53.218 | 53.229 | 37.697 | 23.365 |
| Acetal | 12.579 | 5.448 | 5.817 | 7.618 | 12.731 | 14.451 |
| Acetol | 0.000 | 0.000 | 1.934 | 1.571 | 0.000 | 0.000 |
| Oth | 2.752 | 0362 | 0.484 | 1.322 | 3.364 | 3.743 |
| Unknown | 0.973 | 1.841 | 4.815 | 11.267 | 14.600 | 10.973 |
| Unacct | −6.517 | 11.695 | 16.549 | 16.053 | 28.161 | 44.839 |
| CO* | 7.654 | 2.260 | 1.610 | 2.811 | 7.292 | 8.116 |
| CO2* | 34.807 | 31.257 | 38.411 | 43.490 | 51.091 | 50.576 |
| Sel (%) | | | | | | |
| Acryl | 19.392 | 23.478 | 21.233 | 11.033 | 2.700 | 1.394 |
| Prop | 1.346 | 0.581 | 0.618 | 1.267 | 3.322 | 4.556 |
| 23P | 64.736 | 69.221 | 67.677 | 73.877 | 65.858 | 52.877 |
| Acetal | 11.918 | 6.301 | 7.397 | 10.482 | 22.242 | 32.703 |
| Acetol | 0.000 | 0.000 | 2.460 | 2.162 | 0.000 | 0.000 |
| Oth | 2.607 | 0.419 | 0.615 | 1.819 | 5.878 | 8.471 |

Definitions:

| | |
|---|---|
| Acryl = Acrylic Acid | BOC and BOF - See Table 3 |
| Prop = Propanoic Acid | |
| 23P = 2,3-Pentanedione | |
| Acetal = Acetaldehyde | |
| Acetol = Hydroxyacetone | |

The chemical compound 2,3-pentanedione is formed from lactic acid in a single step in the presence of supported catalysts in a flow reactor system as in Examples 1 to 3; however, other products formed at the same time in parallel and/or consecutive reactions include propanoic acid, acetaldehyde, acrylic acid, hydroxyacetone, and acetic acid. The product mixture also contains a large amount of the water which is used to dilute the lactic acid feed. A separation step was discovered that separates the 2,3-pentanedione from the rest of the compounds in the product mixture giving food-grade 2,3-pentanedione (>93% pure). The separation step has the advantage of efficiently separating 2,3-pentanedione in a single step from most of the product mixture. The scheme separates high boiling acids (acrylic acid, propanoic acid, lactic acid, acetic acid) and hydroxyacetone from low boiling 2,3-pentanedione and acetaldehyde. The acetaldehyde can be easily separated from 2,3-pentanedione utilizing the large difference in their boiling points.

EXAMPLE 4

Figure 3:
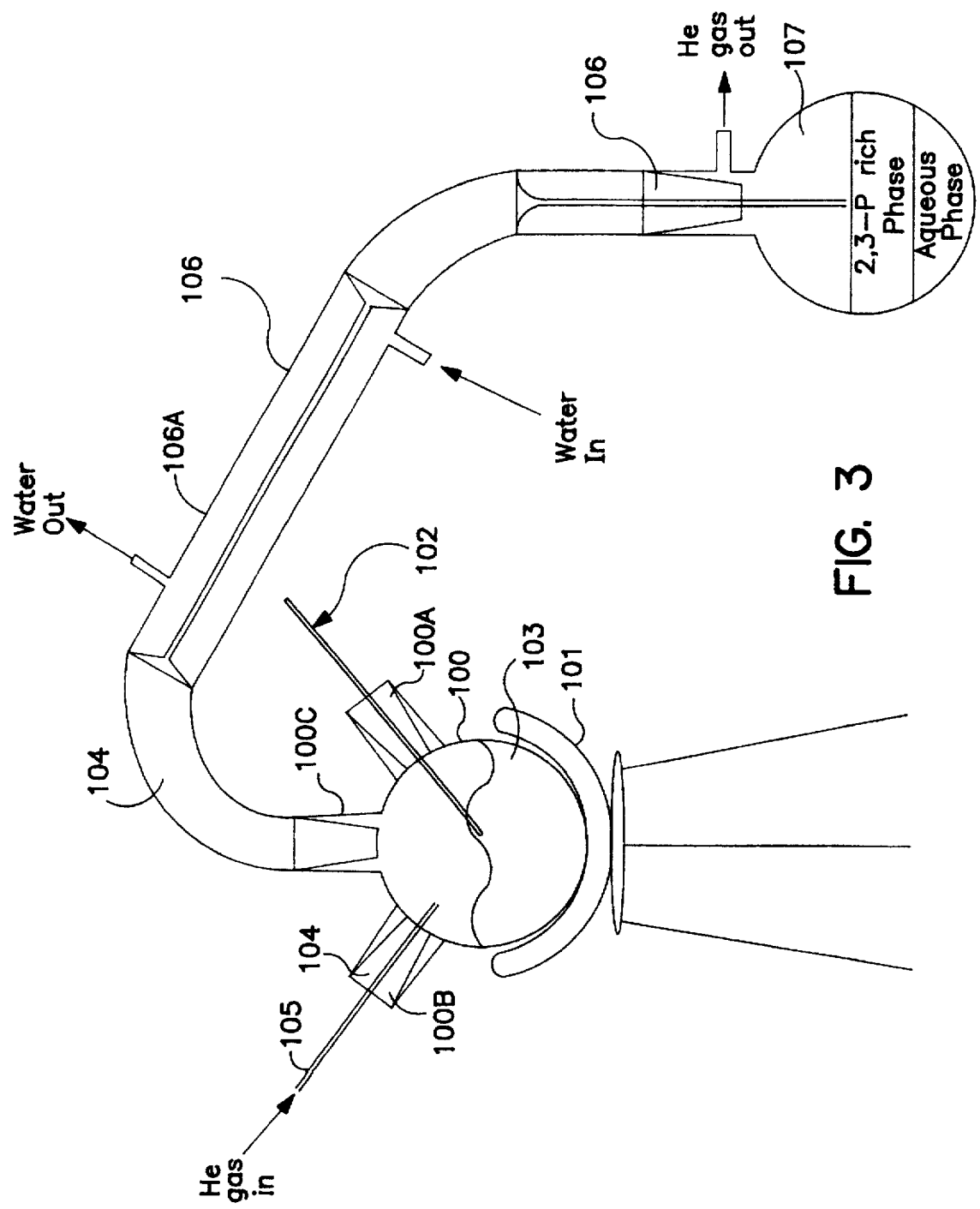
FIG. 3 is a schematic diagram showing an apparatus for separating the 2,3-pentanedione produced in a first step of the reaction over a catalyst.

This Example shows the preferred process for the separation of 2,3-pentanedione from the rest of the product mixture (as in Examples 1 to 3) in a batch distillation system. The separation is carried out in an apparatus such as that shown in FIG. 3. The product mixture is contained in a three-neck round-bottom glass flask 100 that is heated with a heating mantle 101. A thermometer 102 is inserted through one of the necks 101A to measure the temperature of the product mixture 103. The second neck 101B has a glass tube 104 which is kept above the liquid level inside the flask 100 and the other end of which is connected to helium gas line 105. The center neck 100C of the flask is connected to a condenser 106 that is cooled with circulating tap water through jacket 106A. The condensed liquid is collected in a flask 107 attached at the end 106B of the condenser 106.

The 2,3-pentanedione-water system forms an azeotropic mixture that boils at about 80°–91° C. and has a composition of 60–65 mol % water. 2,3-Pentanedione has a very limited solubility in water of 6% by weight at 25° C.; likewise, water solubility in 2,3-pentanedione is less than about 5% by weight at 25° C. When the product mixture is heated, vapors consisting of the azeotropic composition of 2,3-pentanedione and water are formed and are carried with the carrier gas through the condenser 106. Upon cooling and condensation in flask 107, the liquid formed immediately separates into two phases in the collection flask due to the limited solubility of 2,3-pentanedione in water. The top layer consists of mainly 2,3-pentanedione (>93% by wt) and also contains small amounts of water, acetaldehyde, and propanoic acid. If necessary, acetaldehyde can be easily removed by heating this mixture to 30°–35° C. Nearly all the impurities contained in the pentanedione thus purified are chemicals that are allowed in food in much larger amounts.

The only significant trace impurities are acrylic acid and hydroxyacetone.

It is intended that the foregoing description be only illustrative of the present invention and that the present invention be limited only by the hereinafter appended claims.

We claim:

1. A process for the preparation of 2,3-pentanedione which comprises:

(a) contacting a lactic compound selected from the group consisting of lactic acid and lactic acid alkyl esters wherein alkyl contains 1 to 6 carbon atoms in a reaction mixture with a support in the presence of a non-reactive gas at a temperature, wherein the support is heated to between about 250° to 370° C., and at pressures between about 0.1 and 10 MPa, and wherein the contacting is for a period of time which converts the lactic compound to 2,3-pentanedione and other conversion products;

(b) separating the 2,3-pentanedione from the reaction mixture by distillation of the reaction mixture between about 80° to 90° C. to distill an azeotropic mixture of the water and the 2,3-pentanedione from the reaction mixture; and (c) cooling the azeotropic mixture, wherein the 2,3-pentanedione separates from the water and the other conversion products which remain in the water.

2. A process for the preparation of 2,3-pentanedione which comprises:

(a) contacting lactic acid in a reaction mixture containing less than about fifty (50) percent by weight of the lactic acid in water on a support in the presence of a non-reactive gas at a temperature wherein the support is heated to between about 250° and 370° C. and at elevated pressures between about 0.1 and 10 MPa and wherein the contacting is for a period of time which converts the lactic acid to 2,3-pentanedione and other conversion products;

(b) separating the 2,3-pentanedione from the reaction mixture by distillation of the reaction mixture between about 80° to 90° C. to distill an azeotropic mixture of the water and the 2,3-pentanedione from the reaction mixture; and (c) cooling the azeotropic mixture, wherein the 2,3-pentanedione separates from the water and the other conversion products which remain in the water.

3. The process of claim 2 wherein in step (a) the support has a coating of an inorganic compound selected from the group consisting of alkali metal salts and bases which promote the conversion of the lactic acid to the 2,3-pentanedione.

4. The process of any one of claims 1 or 2 wherein in step (a) the contacting is by flowing the reaction mixture over the support.

5. The process of claim 2 wherein in step (a) the reaction mixture is maintained at a pressure of between about 0.4 to 8 MPa.

6. The process of claim 3 wherein in step (a) the inorganic compound is selected from the group consisting of a potassium salt, a cesium salt, potassium hydroxide, cesium hydroxide and mixtures thereof.

7. The process of claim 3 wherein in step (a) the inorganic compound is selected from the group consisting of cesium nitrate, cesium hydroxide, potassium hydroxide, potassium nitrate, potassium phosphate and mixtures thereof.

8. A process for the preparation of 2,3-pentanedione which comprises:

(a) contacting a lactic compound selected from the group consisting of lactic acid and lactic acid alkyl esters, wherein alkyl contains 1 to 6 carbon atoms in a reaction mixture with a support containing an inorganic compound selected from the group consisting of potassium and cesium salts and bases and mixtures of the salts and bases in the presence of a non-reactive gas, at a temperature wherein the support is heated to between about 250° and 370° C. and at pressures between about 0.1 and 10 MPa and wherein the contacting is for a period of time which converts the lactic compound to 2,3-pentanedione with an overall yield of at least about 40% and a selectivity of at least about 60%; and (b) separating the 2,3-pentanedione from the reaction mixture.

9. A process for the preparation of 2,3-pentanedione which comprises:

(a) contacting lactic acid in a reaction mixture containing less than about fifty (50) percent by weight of the lactic acid in water on a support containing inorganic compound selected from the group consisting of potassium and cesium salts and bases and mixtures of the salts and bases in the presence of a non-reactive gas at a temperature wherein the support is heated to between about 250° and 370° C. and at a pressure between about 0.1 and 10 MPa and wherein the contacting is for a period of time which converts the lactic acid to 2,3-pentanedione with an overall yield of at least 40% and a selectivity of at least about 60%; and (b) separating the 2,3-pentanedione from the reaction mixture.

10. The process of claim 9 wherein in step (a) the support has a coating of the inorganic compound.

11. The process of claim 9 wherein in step (a) the compound is selected from the group consisting of cesium nitrate, cesium hydroxide, potassium hydroxide, potassium nitrate, potassium phosphate and mixtures thereof.

* * * * *

UNITED STATES PATENT AND TRADEMARK OFFICE
CERTIFICATE OF CORRECTION

PATENT NO. : 5,731,471
DATED : March 24, 1998
INVENTOR(S) : Dennis J. Miller, et al.

It is certified that error appears in the above-indentified patent and that said Letters Patent is hereby corrected as shown below:

On the title page, item [56]:

Under "Other Publications", The correct citation for Gunter, et al. is --252-260--, rather than "252-250".

Columns 7 and 8, Table 2, 2nd column for "CO", "0.1" should be --1.1--.

Columns 7 and 8, Table 2, 7th column heading, a closed parenthesis ")" should be inserted after "(empty reactor".

Columns 9 and 10, Table 3, 5th column heading "80" should be --(80)--.

Columns 9 and 10, Table 4, 2nd column, 1st row, "9/9(2)" should be --9.9(2)--.

Columns 9 and 10, Table 4, 5th column heading, "80" should be --(80)--.

Column 12, Table 5, 1st column, 4th row, "acetadehyde" should be --acetaldehyde--.

Column 12, Table 5, 4th column, 2nd row, "18(9)" should be --1.8(9)--.

Columns 13 and 14, Table 6, 7th column, 1st row, "10.9(2.0)" should be --10.9(20)--.

UNITED STATES PATENT AND TRADEMARK OFFICE
CERTIFICATE OF CORRECTION

Page 2 of 3

PATENT NO. : 5,731,471
DATED : March 24, 1998
INVENTOR(S) : Dennis J. Miller, et al.

It is certified that error appears in the above-indentified patent and that said Letters Patent is hereby corrected as shown below:

Column 16, Table 7, 4th column, 10th row, "5.147" should be --5.747--.

Columns 17 and 18, Table 7, 5th column for "CO2*", "51.556" should be --57.556--.

Columns 17 and 18, Table 7, 3rd column for "Prop", "0.893" should be --0.803--.

Columns 19 and 20, Table 7, 4th column, line 29, "1.1219" should be --1.11º -.

Columns 19 and 20, Table 7, 5th column, line 39, "49.911" should be --49.011--.

Columns 19 and 20, Table 7, 6th column, line 51, "3.00" should be --3.000--.

Columns 21 and 22, Table 7, 2nd column, line 27, "21.133" should be --21.113--.

Columns 21 and 22, Table 7, 6th column, line 34, "28.6.81" should be --28.681--.

Columns 21 and 22, Table 7, 2nd column, line 58, "-12.918" should be -- -12.978--.

Columns 21 and 22, Table 7, 3rd column, line 73, "17.318" should be --17.378--.

UNITED STATES PATENT AND TRADEMARK OFFICE
CERTIFICATE OF CORRECTION

PATENT NO. : 5,731,471
DATED : March 24, 1998
INVENTOR(S) : Dennis J. Miller, et al.

It is certified that error appears in the above-indentified patent and that said Letters Patent is hereby corrected as shown below:

Columns 23 and 24, Table 7, 6th column, line 6, "2509" should be --2.509--.

Columns 23 and 24, Table 7, 3rd column, line 27, "0362" should be --0.362--.

Signed and Sealed this

Eleventh Day of August 1998

Attest:

BRUCE LEHMAN

Attesting Officer

Commissioner of Patents and Trademarks